United States Patent [19]

Levorse, Jr.

[11] Patent Number: 5,276,176

[45] Date of Patent: Jan. 4, 1994

[54] COMPOSITIONS CONTAINING HIGH PROPORTION OF ALPHA,3,3-TRIMETHYL-1-CYLCLOHEXEN-1-METHANOL DERIVATIVE, ORGANOLEPTIC USES THEREOF AND PROCESS FOR PREPARING SAME

[75] Inventor: Anthony T. Levorse, Jr., Old Bridge, N.J.

[73] Assignee: International Flavors & Fragrances Inc., New York, N.Y.

[21] Appl. No.: 2,235

[22] Filed: Jan. 8, 1993

Related U.S. Application Data

[62] Division of Ser. No. 920,817, Jul. 28, 1992, Pat. No. 5,234,902.

[51] Int. Cl.$^5$ .............................................. C07C 69/74
[52] U.S. Cl. ...................................... 560/128; 568/361; 568/820
[58] Field of Search ................ 560/128; 568/361, 820

[56] References Cited

U.S. PATENT DOCUMENTS

| | | | |
|---|---|---|---|
| 3,847,975 | 11/1974 | Hall | 252/522 |
| 4,147,672 | 4/1979 | Schulte-Elte et al. | 252/522 |
| 4,264,467 | 4/1981 | Schulte-Elte et al. | 252/174.11 |
| 4,289,659 | 9/1981 | Schulte-Elte et al. | 252/522 R |

FOREIGN PATENT DOCUMENTS 852918  7/1977  Belgium ............................ 568/376

*Primary Examiner*—James H. Reamer
*Attorney, Agent, or Firm*—Arthur L. Liberman

[57] ABSTRACT

Described are alpha, 3,3-trimethyl-1-cyclohexen-1-methanol derivative-containing composition having from about 85 up to about 90% by weight of a compound having the structure:

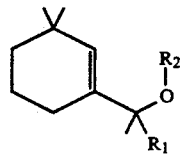

and from about 10 up to about 15% by weight of a compound having the structure:

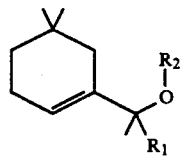

wherein $R_1$ is hydrogen or methyl and $R_2$ is hydrogen or acetyl with the proviso that when $R_1$ is methyl, $R_2$ is hydrogen; and uses thereof in augmenting or enhancing the aroma of perfume compositions, colognes and perfumed articles including but not limited to solid or liquid anionic, cationic, nonionic or zwitterionic detergents, fabric softener compositions, fabric softener articles and hair preparations; as well as processes for preparing said alpha, 3,3-trimethyl-1-cyclohexen-1-methanol derivative-containing composition.

1 Claim, 12 Drawing Sheets

GLC PROFILE FOR EXAMPLE I.
CRUDE

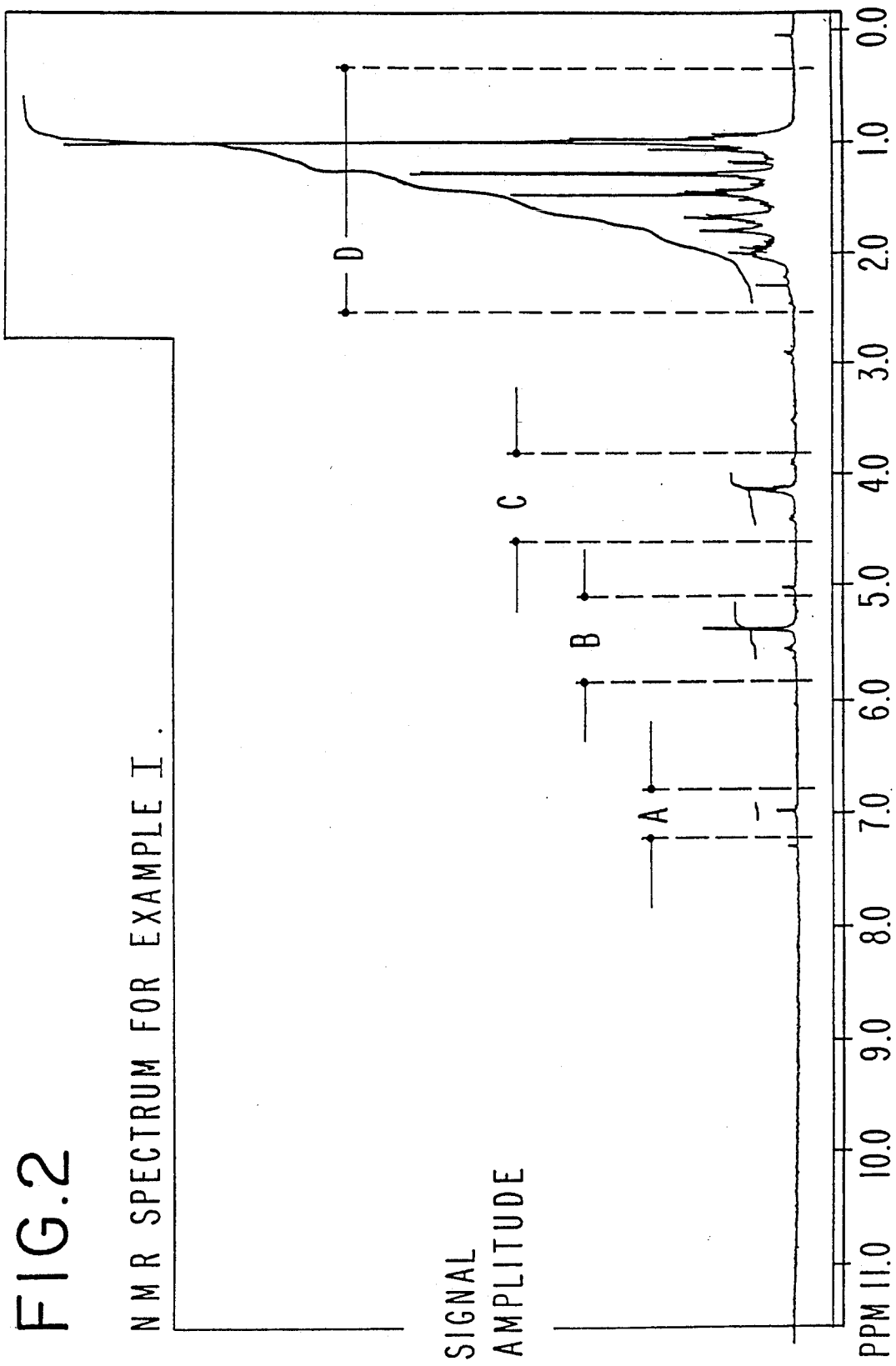
FIG.2 NMR SPECTRUM FOR EXAMPLE I.

FIG.2-A
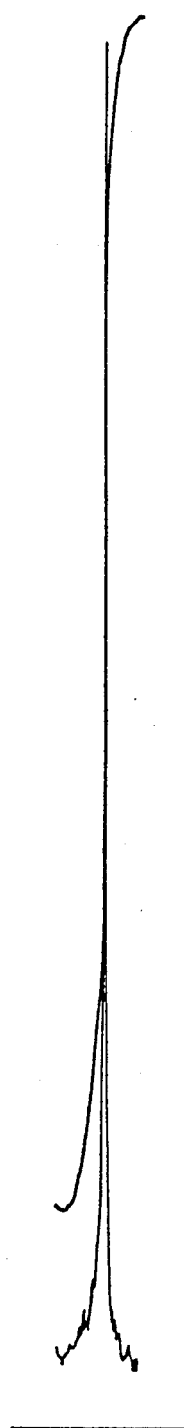
7.0
PPM
FIG.2-B
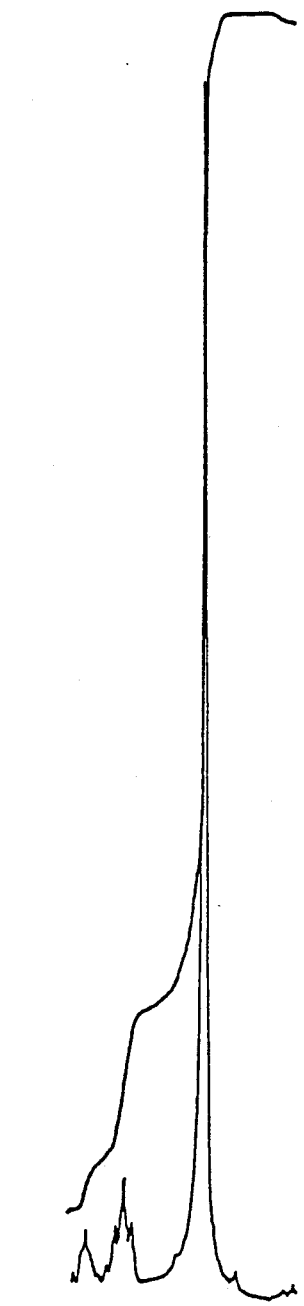
5.6 5.4 5.2
PPM

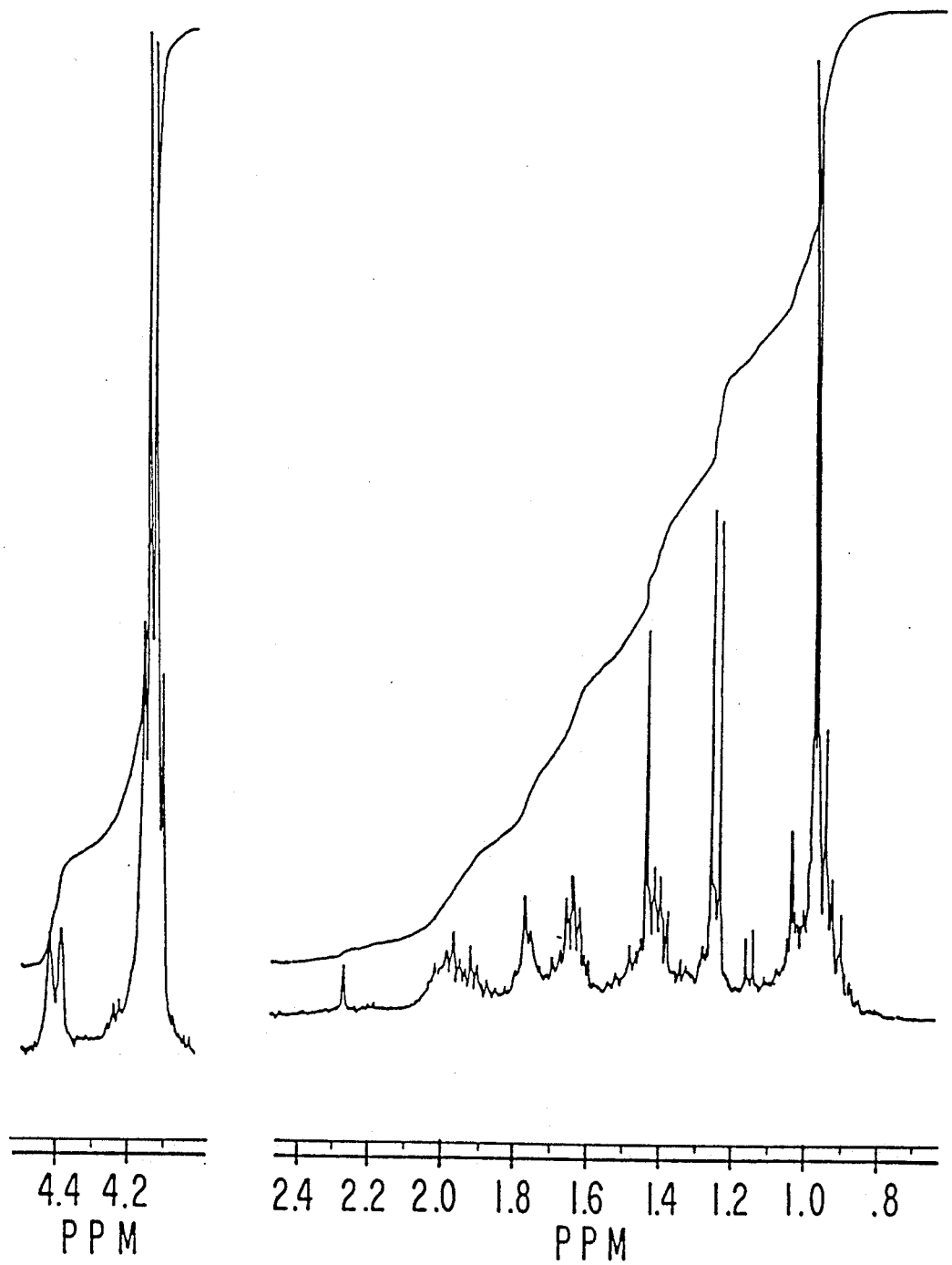

FIG.4-A  FIG.4-B
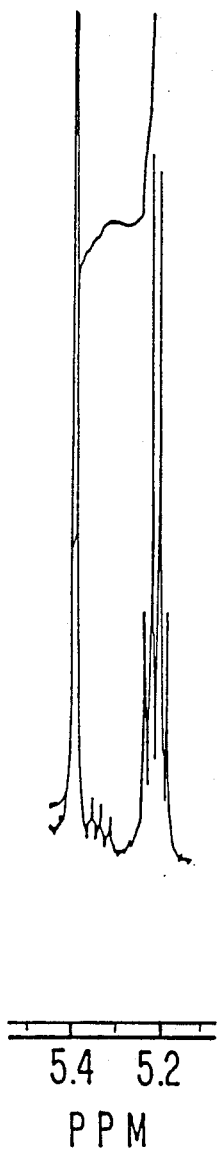
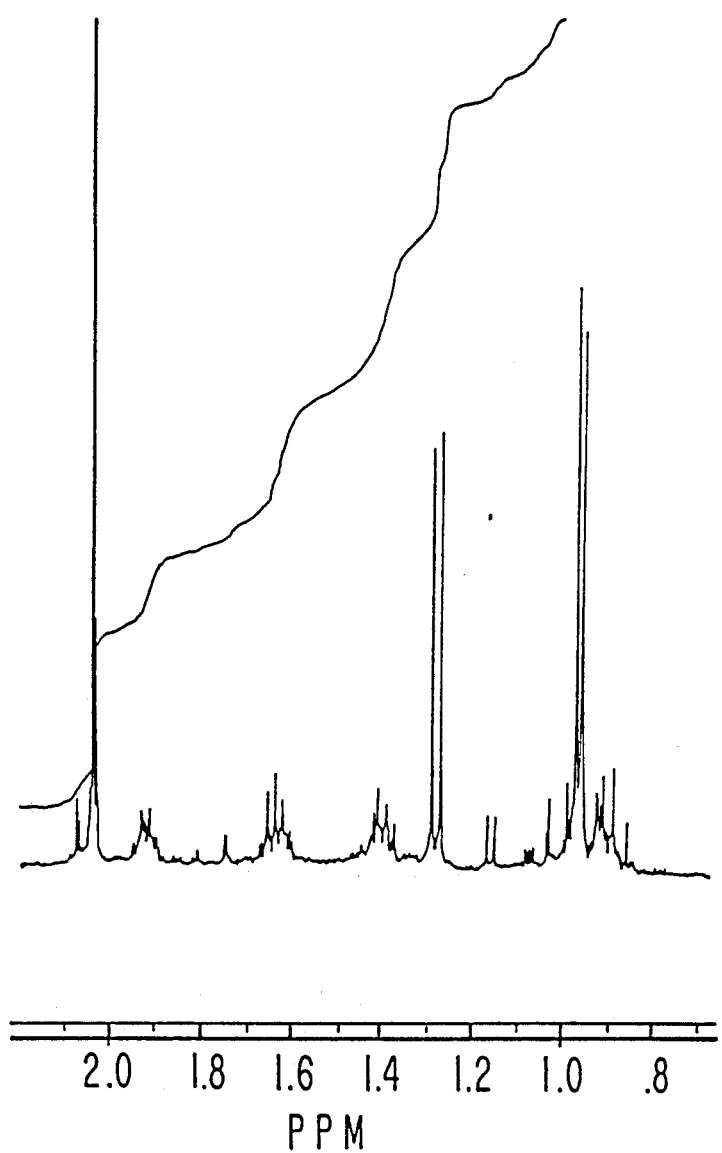

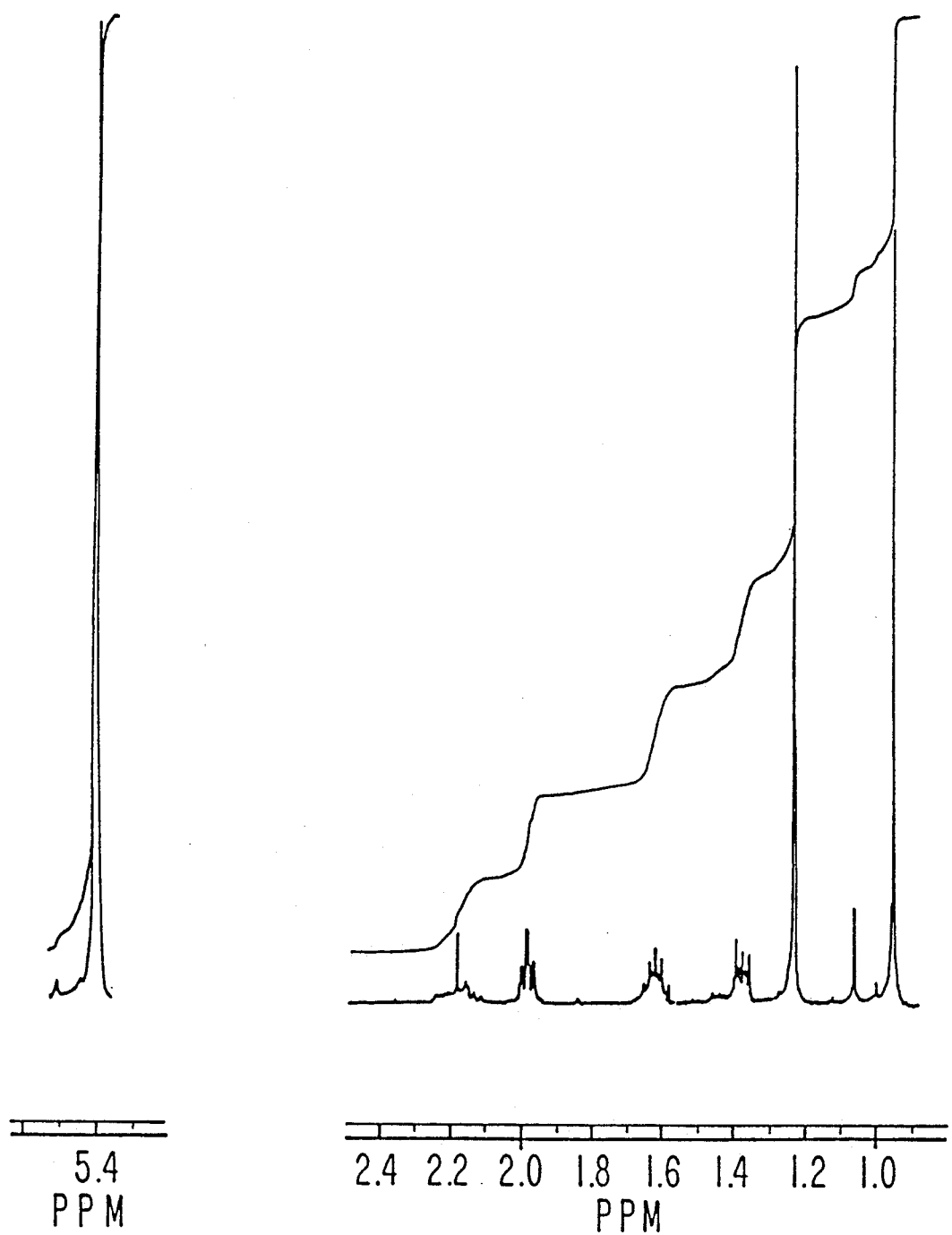

COMPOSITIONS CONTAINING HIGH PROPORTION OF ALPHA,3,3-TRIMETHYL-1-CYLCLOHEXEN-1-METHANOL DERIVATIVE, ORGANOLEPTIC USES THEREOF AND PROCESS FOR PREPARING SAME

This is a divisional of U.S. patent application Ser. No. 920,817, filed Jul. 28, 1992 U.S. Pat. No. 5,234,902.

BACKGROUND OF THE INVENTION

The instant invention relates to alpha, 3,3-trimethyl-1-cyclohexen-1-methanol derivative-containing composition containing from about 85 up to about 90% by weight of a compound defined according to the structure:

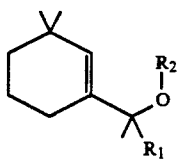

and from about 10 up to about 15% by weight of a compound defined according to the structure:

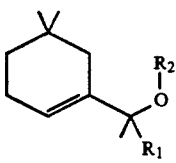

wherein $R_1$ is hydrogen or methyl and $R_2$ is hydrogen or acetyl with the proviso that when $R_1$ is methyl, $R_2$ is hydrogen and uses of same in augmenting or enhancing the aroma of perfume compositions, perfumed articles and colognes.

Inexpensive chemical compounds which can provide rose, camphoraceous, fruity, woody, green, patchouli, earthy and minty aromas with rose, apple, amber and animalic topnotes and green and woody undertones are highly desirable in the art of perfumery. Many of the natural materials which provide such fragrances and contribute such desired nuances to perfume compositions as well as perfumed articles are high in cost, unobtainable at times, vary in quality from one batch to another and/or are generally subject to the usual variations of natural products.

There is, accordingly, a continuous effort to find synthetic materials which will replace, enhance or augment the fragrance notes provided by natural essential oils or compositions thereof. Unfortunately, many of the synthetic materials have the desired nuances only to a relatively small degree or they contribute undesirable or unwanted odor to the composition.

Cycloalkylalkanols are well known in the prior art and their utilities are known in perfumery.

Belgian Patent 852918 and corresponding Italian Patent No. 1,058,547 disclose the cyclization of dehydrolinalool using polyphosphoric acid to produce 3,3-dimethyl-1-acetyl-1-cyclohexene according to the reaction:

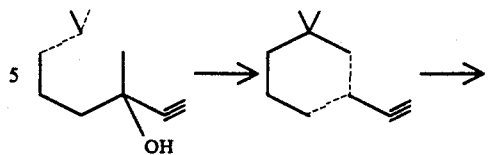

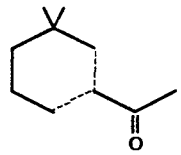

wherein, in the structures:

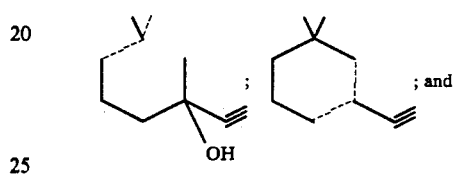

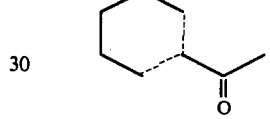

these structures are representative of mixtures wherein, in the mixtures one of the dashed lines represents a carbon-carbon double bond and the other of the dashed lines represents a carbon-carbon single bond. The said Belgian and Italian Patents indicate that the compounds defined according to the structure:

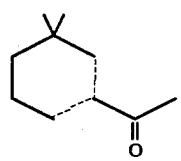

are useful in perfumery. Also, U.S. Pat. No. 4,147,672 issued on Apr. 3, 1979; U.S. Pat. No. 4,264,467 issued on Apr. 28, 1981 and U.S. Pat. No. 4,289,659 issued on Sep. 15, 1981 disclose the preparation of the compounds having the structures:

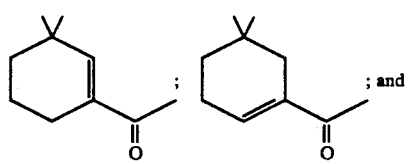

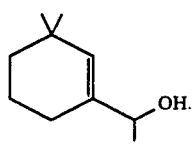

U.S. Pat. No. 3,847,975 issued on Nov. 12, 1974 discloses the use of the compound having the structure:

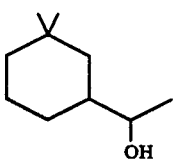

as a perfumant.

Nothing in the prior art discloses the alpha, 3,3-trimethyl-1-cyclohexen-1-methanol derivative-containing composition containing a high proportion of compounds defined according to the structure:

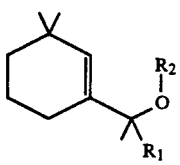

(e.g., 85-90%) and a significantly low proportion of compounds having the structure:

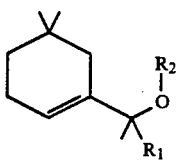

(e.g., 10-15%) wherein $R_1$ is hydrogen or methyl and $R_2$ is hydrogen or acetyl with the proviso that when $R_1$ is methyl, $R_2$ is hydrogen.

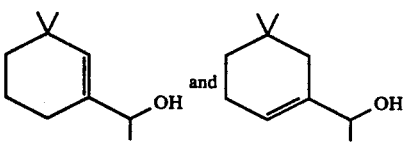

with a weight ratio of compound having the structure:

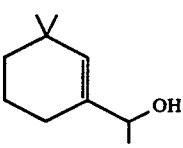

to compound having the structure:

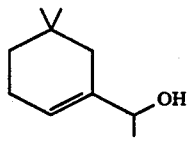

being 85:15.

FIG. 2 is the NMR spectrum for the compound having the structure:

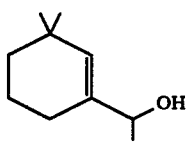

prepared according to Example I.

FIGS. 2A, 2B, 2C and 2D are detailed sections indicated by the letters "A", "B", "C" and "D" of FIG. 2.

Figure 3:
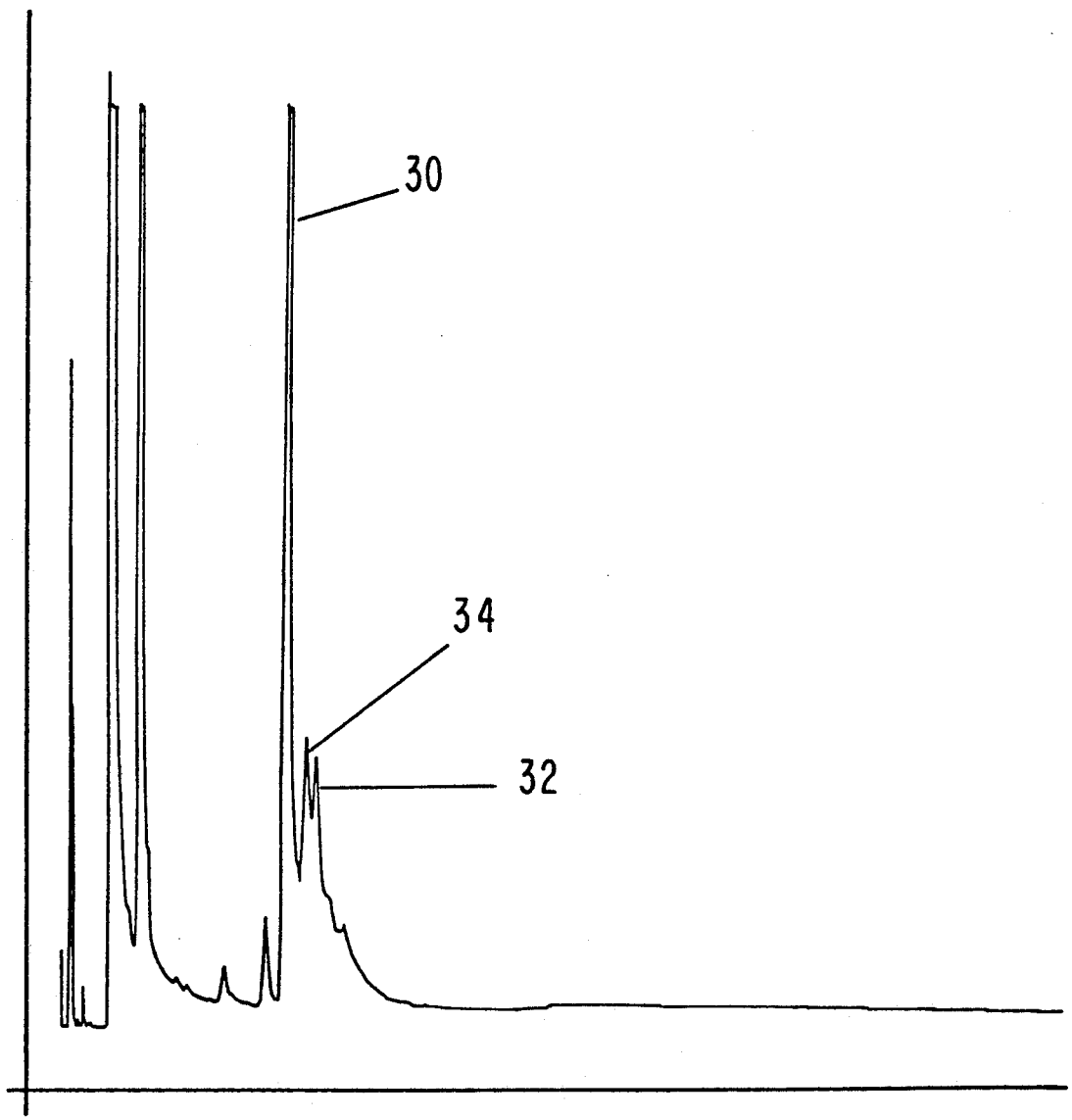

FIG. 3 is the GLC profile for the crude reaction product of Example II containing the compounds having the structures:

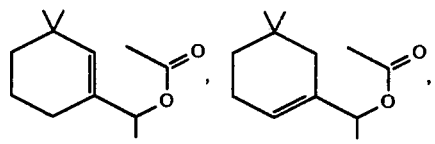

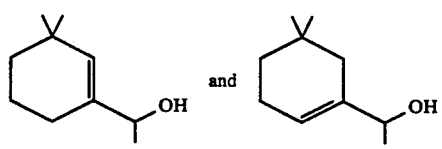

with the ratio of the compound having the structure:

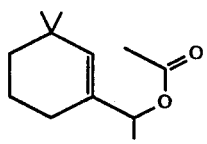

to the compound having the structure:

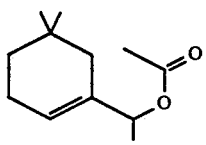

being 85:15.

Figure 4:
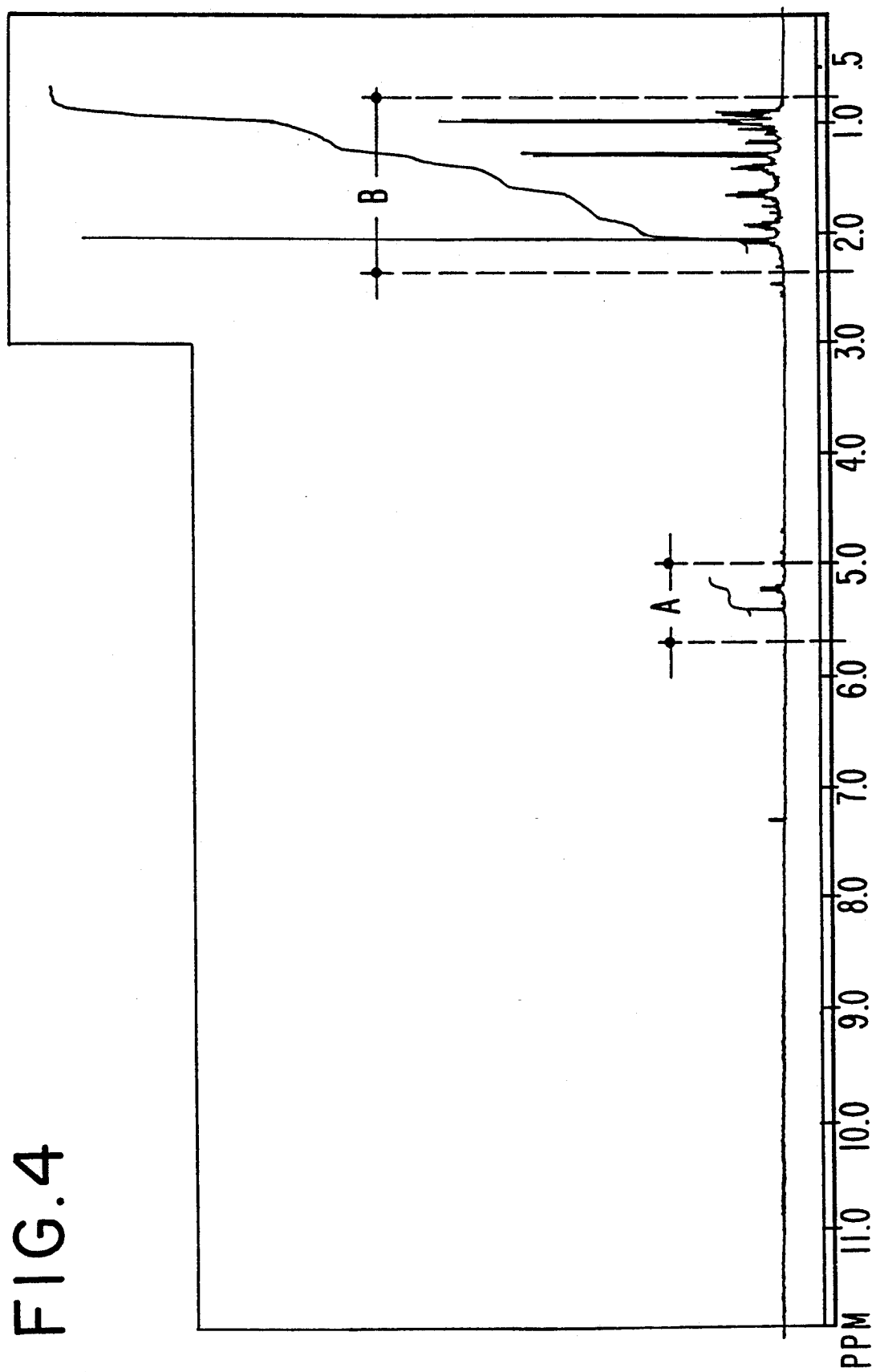

FIG. 4 is the NMR spectrum for the compound having the structure:

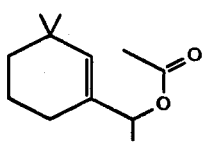

prepared according to Example II.

FIGS. 4A and 4B are detailed sections indicated by the letters "A" and "B" on FIG. 4.

Figure 5:
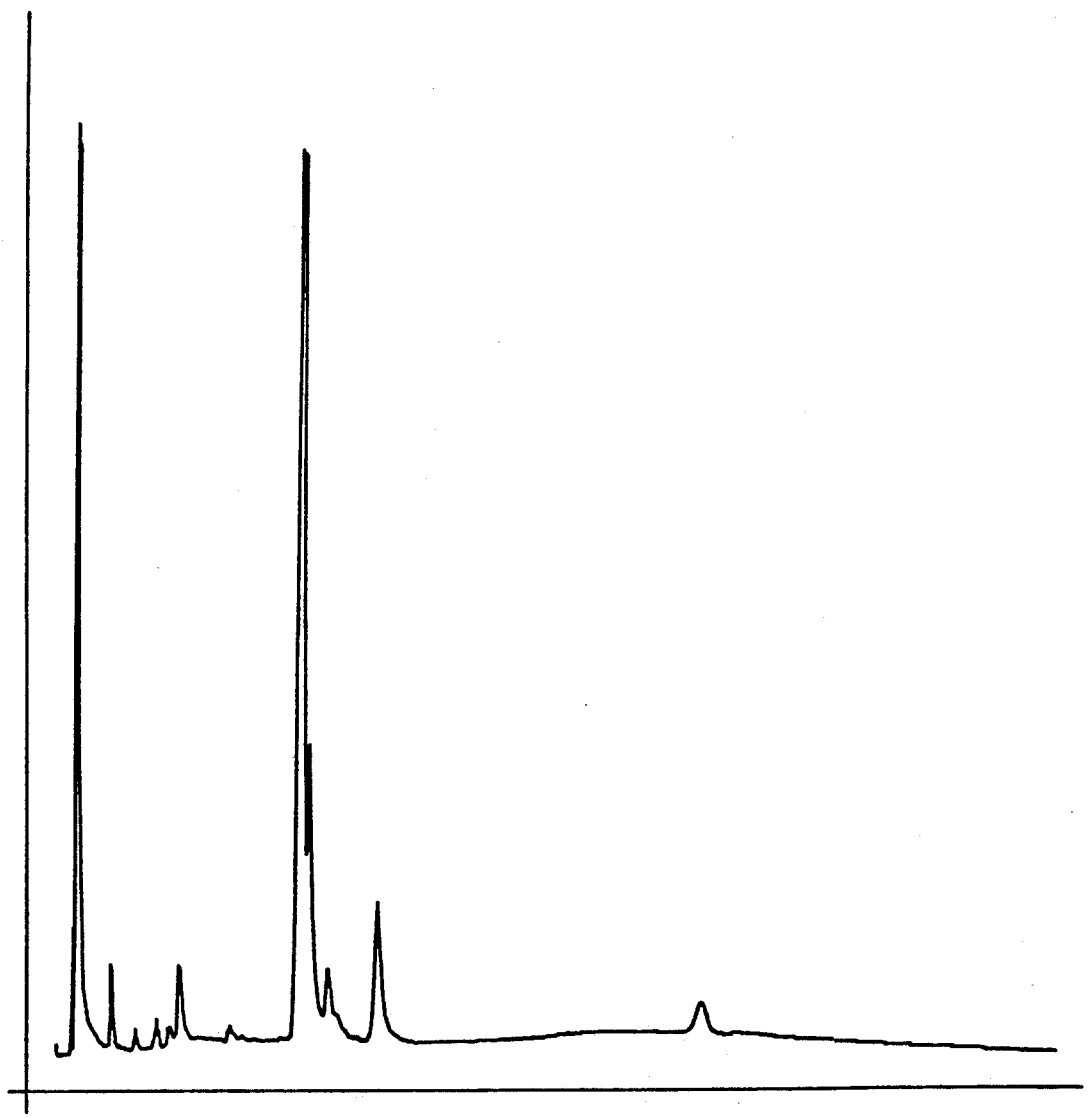

FIG. 5 is the GLC profile for the crude reaction product of Example III containing the compounds having the structures:

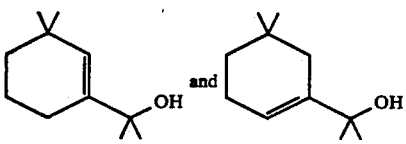

with the ratio of the compound having the structure:

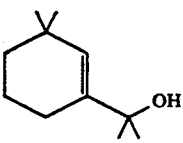

to the compound having the structure:

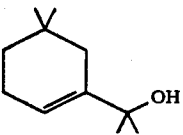

being 85:15.

Figure 6:
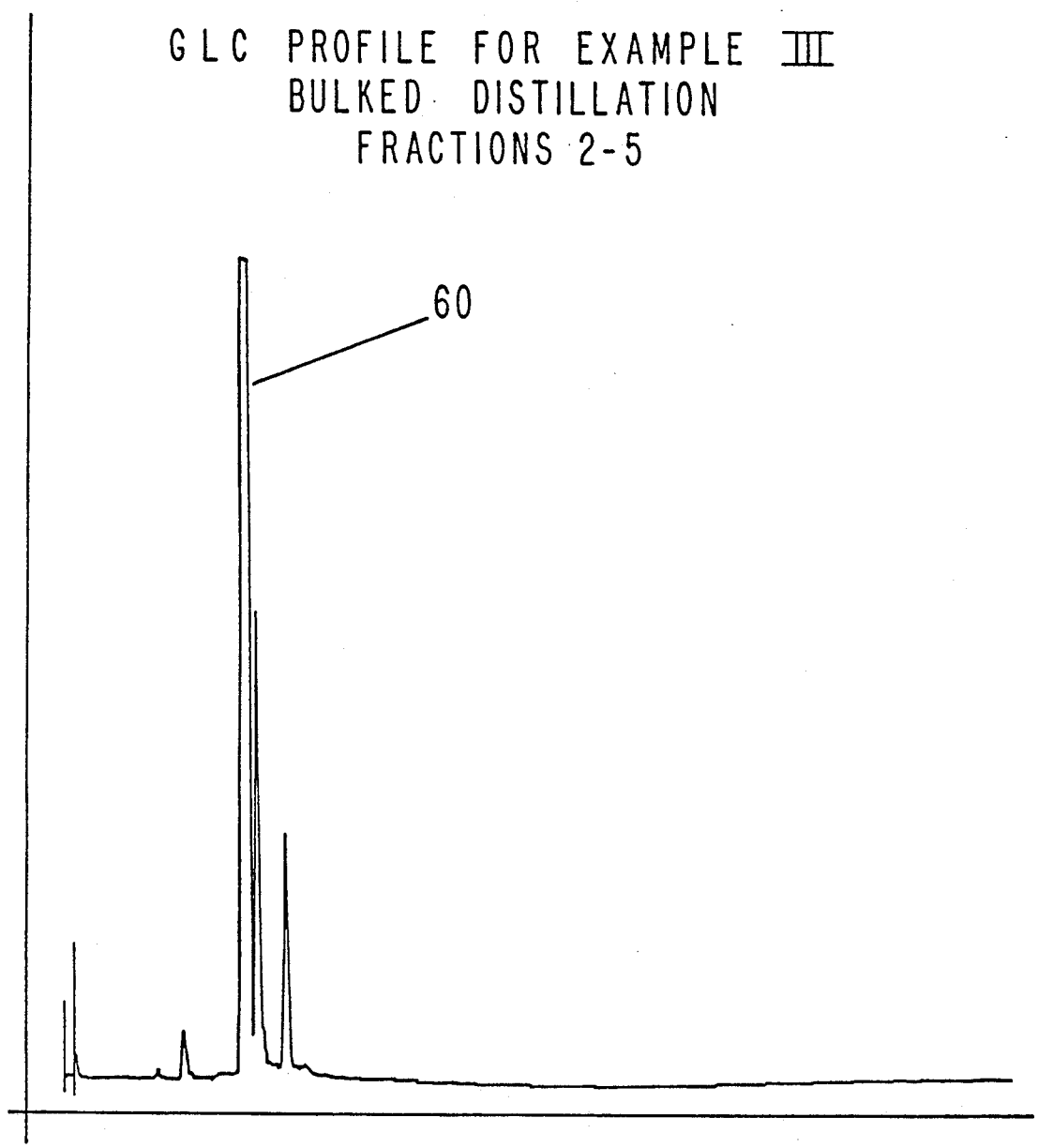

FIG. 6 is the GLC profile for bulked distillation fractions 2-5 of the distillation product of the reaction product of Example III containing the compounds having the structures:

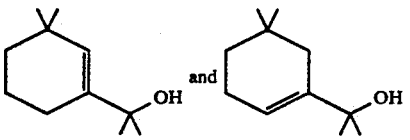

with the ratio of compound having the structure:

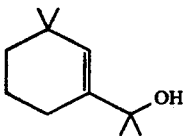

to the compound having the structure:

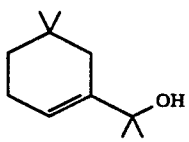

being 85:1.

Figure 7:
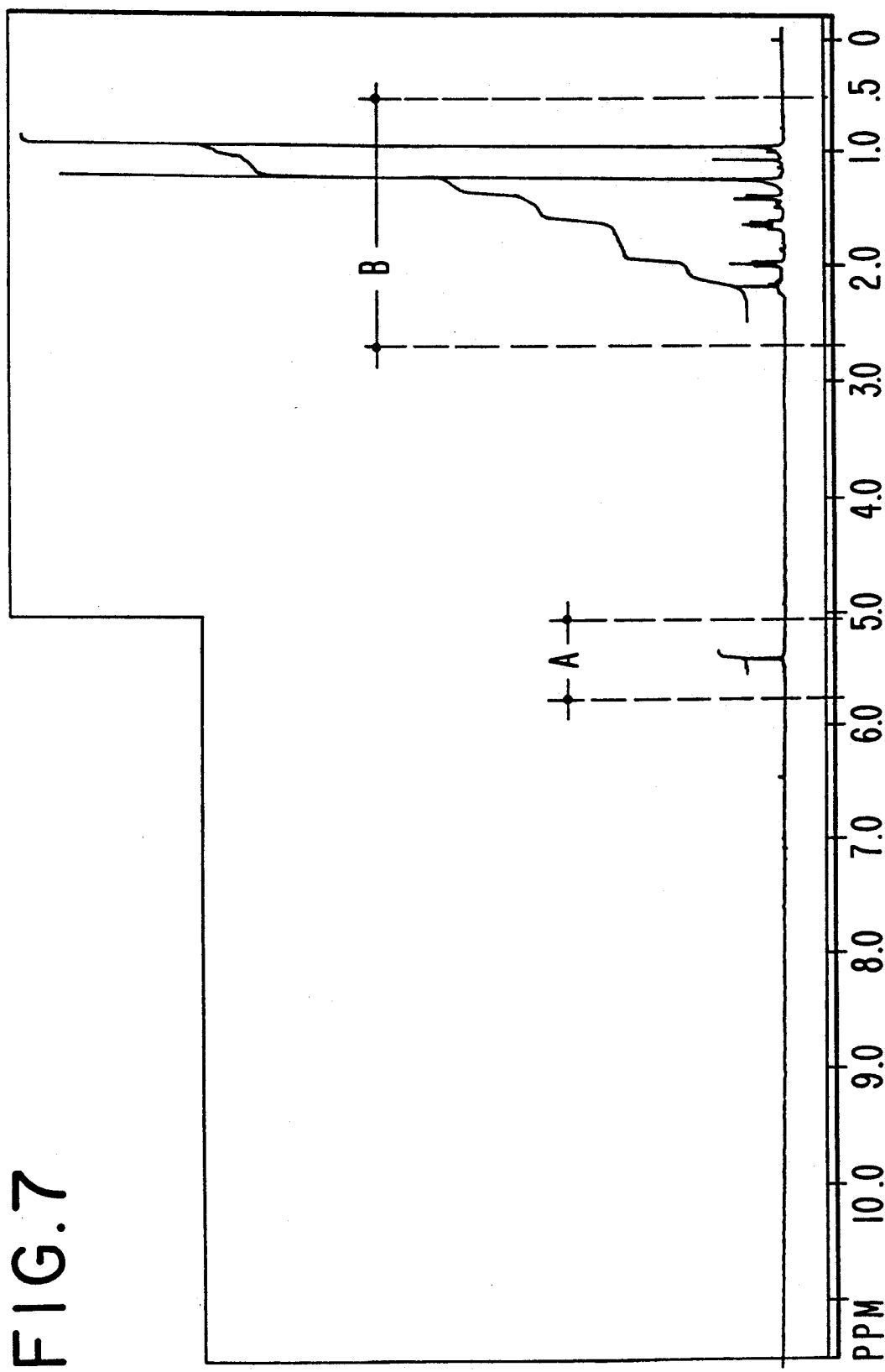

FIG. 7 is the NMR spectrum for the compound having the structure:

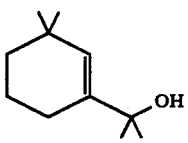

prepared according to Example III.

FIGS. 7A and 7B are detailed sections indicated by the letters "A" and "B" of the NMR spectrum, FIG. 7.

Figure 8:
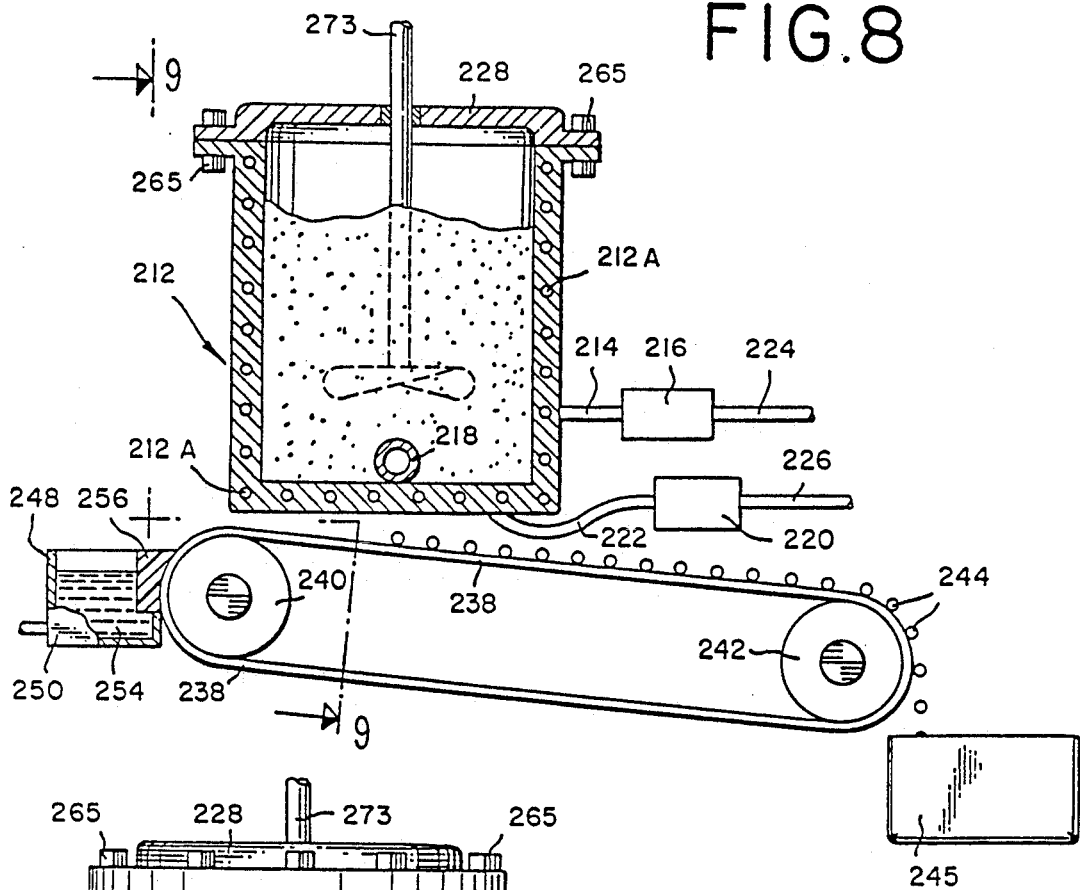

FIG. 8 is a partial side elevation view and partial sectional view of an apparatus for forming polymer pellets containing at least one of the alpha, 3,3-trimethyl-1-cyclohexen-1-methanol derivative-containing composition of my invention.

Figure 9:
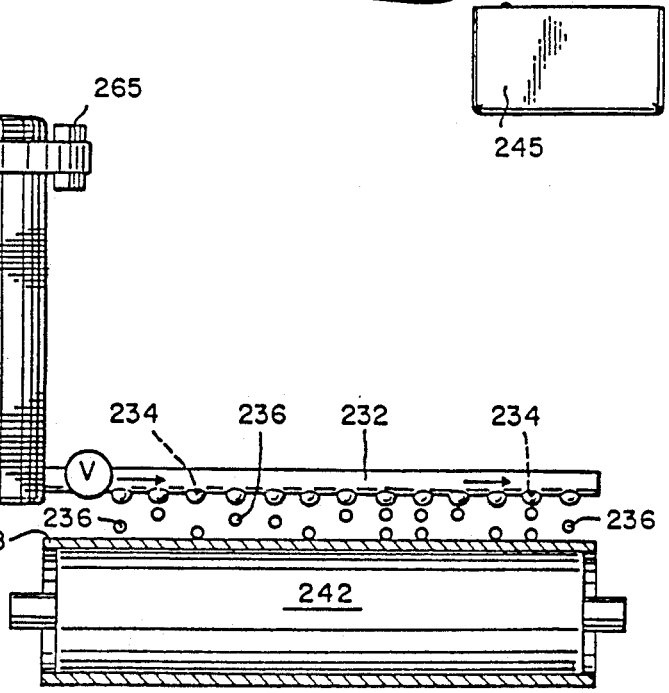

FIG. 9 is a section taken along the line 9—9 of FIG. 8.

DETAILED DESCRIPTION OF THE DRAWINGS

Referring to FIGS. 8 and 9, the apparatus used in producing polymeric fragrances containing at least one of the alpha, 3,3-trimethyl-1-cyclohexen-1-methanol derivative-containing composition of my invention comprises a device for forming scented polyolefin (for example) pellets, which comprises a vat or container 212 into which a mixture of polyolefin such as polyethylene and an aromatic substance or scented material is placed (in this case at least one of the alpha, 3,3-trimethyl-1-cyclohexen-1-methanol derivative-containing composition of my invention).

The container is closed by an air-tight lid 228 and the air-tight lid 228 is clamped to the container 212 by bolts 265.

A stirrer 273 traverses the lid or cover 228 in an air-tight manner and is rotated in a suitable manner.

Container 212 having heating coils 212A which are supplied with electric current through cable 224 from a rheostat or control 216 is operated to maintain a temperature inside the container 212 such that polyethylene or other thermoplastic polymer in the container will be maintained in the molten or liquid state. It has been found advantageous to employ a colorless, odorless polymer (e.g., polyethylene) with viscosity ranging between 180 and 220 saybolt seconds and having a melting point in the range of 220°-280° F. The heater 212A is operated to maintain the upper portion of the container 212 within a temperature range of from 250°-350° F. The bottom portion of the container is heated by means of heating coils 212A heated through control 220 connected thereto through a connecting wire 222 to maintain the lower portion of the container within a temperature range of from 250° 350° F.

Thus, polymer (e.g., polyethylene) is added to container 212 and is heated from 10-12 hours whereafter a scented aroma imparting material (at least one of the alpha, 3,3-trimethyl-1-cyclohexen-1-methanol derivative-containing composition of my invention) is added quickly to the melt. The material must be compatible with the polyolefin and forms a homogeneous liquid melt therewith. The scented material is of a type for the particular aroma desired and formulated specifically for the scenting purpose for which the polyolefin will be employed.

Generally, about 5-30% by weight of the scented material (containing at least one of the alpha, 3,3-trimethyl-1-cyclohexen-1-methanol derivative-containing composition of my invention) are added to the polyolefin.

After the scent imparting material (e.g., a composition containing at least one of the alpha, 3,3-trimethyl-1-cyclohexen-1-methanol derivative-containing composition of my invention) is added to the container 212, the mixture is stirred for a few minutes, for example, 5-15 minutes, and maintained within the temperature range as indicated, supra, by means of heating coils 212A.

The controls 216 and 220 are connected, respectively, through cables 214 and 222, respectively, to heating coils 212A. The said controls 216 and 220 are also connected through cables 224 and 226, respectively, to a suitable power supply of electric current for supplying the electric power to the heating coils 212A for heating purposes.

Thereafter, the valve "V" is opened permitting the mass to flow outwardly through conduit 218/232 having a multiplicity of orifices 234, adjacent to the lower side thereof. The outer end of the conduit 218/232 is closed so that the liquid polymer (e.g., polyolefin) and aroma imparting material (e.g., at least one of the alpha, 3,3-trimethyl-1-cyclohexen-1-methanol derivative-containing composition of my invention) will continuously drop through orifices 234 downwardly from conduit 232. During this time the temperature of the polymer (e.g., polyolefin) and scent imparting material (e.g., a mixture containing at least one of the alpha, 3,3-trimethyl-1-cyclohexen-1-methanol derivative-containing composition of my invention) is accurately controlled so that a temperature in the range of from about 210°-275° F. will exist in the conduit 218/232. The regulation of the temperature through the controls 216 and 220 is essential in order to insure temperature balance to provide for the continuous dropping or dripping of molten polymer (e.g., polyethylene) and scenting material (e.g., one or more of the alpha, 3,3-trimethyl-1-cyclohexen-1-methanol derivative-containing composition of my invention) mixture through the orifices 234 at a rate which will insure the formation of droplets 236 which will fall downwardly onto a moving conveyor belt 238 caused to run between conveyor wheels 240 and 242 beneath the conduit 232.

When the droplets 236 fall onto the conveyor 238 they form pellets 244 which harden almost instantaneously and fall off the end of the conveyor 238 into a container 245 and utilized in a process as illustrated, infra.

A feature of this aspect of the process of my invention is the provision for moistening the conveyor belt 238 to insure rapid formation of the solid polymeric (e.g., polyolefin) scented pellets 244 without sticking to the belt. The belt 238 is advantageously fabricated of a material which will not normally stick to a melted plastic but a moistening means 248 insures a sufficiently cold temperature of the belt surface for an adequate formation of the pellets 244. The adequate moistening means comprises a container 250 which is continuously fed with water 254 to maintain a level for moistening a sponge element 256 which bears against the exterior of the belt 238.

FIG. 2 is the NMR spectrum for the compound having the structure:

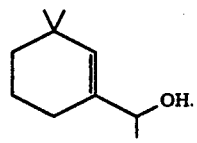

The sections indicated by the letters "A", "B", "C" and "D" are, respectively, shown in enlarged drawings in FIGS. 2A, 2B, 2C and 2D.

FIG. 3 is the GLC profile for the crude reaction product of Example II. The peak indicated by reference numeral 30 is the peak for the mixture of isomers having the structures:

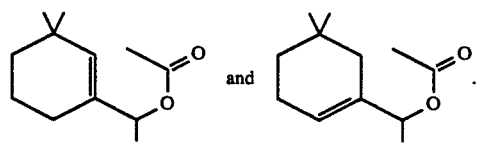

Peaks 32 and 34 are for the isomers having the structures:

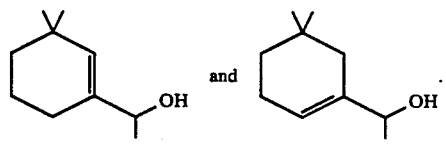

FIG. 4 is the NMR spectrum for the compound having the structure:

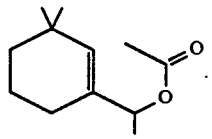

The sections indicated by the letters "A" and "B" are shown in enlarged form respectively in FIGS. 4A and 4B.

FIG. 6 is the GLC profile for bulked distillation fractions 2-5 of the distillation product of the reaction product of Example III containing the compounds having the structures:

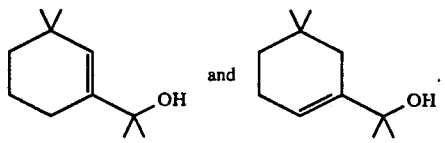

The peak indicated by reference numeral 60 is the peak for the mixture of compounds having the structures:

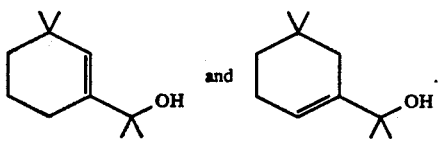

FIG. 7 is the NMR spectrum for the compound having the structure:

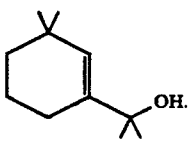

The sections of the NMR spectrum indicated by the letters "A" and "B" are, respectively, shown in enlarged form in FIGS. 7A and 7B, respectively.

THE INVENTION

The present invention provides alpha, 3,3-trimethyl-1-cyclohexen-1-methanol derivative-containing composition containing compounds having the structures:

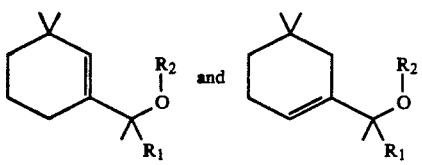

wherein the compounds having the structure:

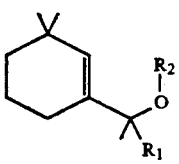

are in an amount in the compositions of from 85 to 90% and wherein the compounds having the structure:

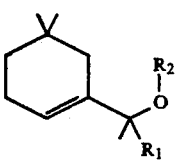

are in the amount of from 10–15% in the compositions; and further, wherein $R_1$ is hydrogen or methyl and $R_2$ is hydrogen or acetyl with the proviso that when $R_1$ is methyl $R_2$ is hydrogen; as well as organoleptic uses of said compositions.

The compositions of matter of my invention produced according to the process of my invention are capable of augmenting, enhancing or providing rose, camphoraceous, fruity, woody, green, patchouli, earthy and minty aromas, with rose, apple, amber and animalic topnotes and with green and woody undertones to perfume compositions, colognes and perfumed articles (e.g., solid or liquid anionic, cationic, nonionic or zwitterionic detergents, fabric softener articles, drier-added fabric softener articles, fabric softener compositions, cosmetic powders, hair preparations, perfumed polymers, room deodorants and the like).

The alpha, 3,3-trimethyl-1-cyclohexen-1-methanol derivative-containing composition of my invention are prepared by means of first reacting dehydrolinalool, a mixture of compounds having the structures:

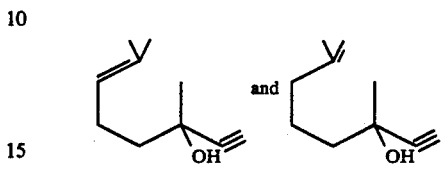

with a dehydrating agent such as phosphoric acid or polyphosphoric acid at a temperature in the range of from about 50° C. up to about 170° C. according to the reaction:

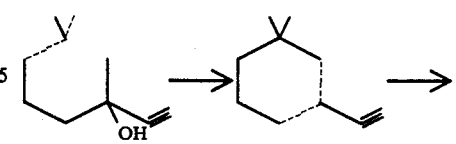

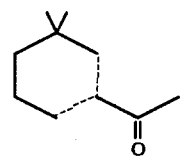

wherein the compounds having the structures:

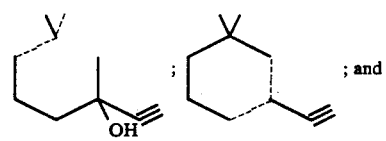

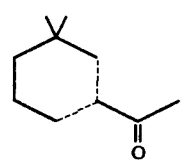

are indicative of mixtures of compounds wherein in the mixtures one of the dashed lines represents a carbon-carbon double bond and the other of the dashed lines represent carbon-carbon single bonds.

The resulting compounds defined according to the structure:

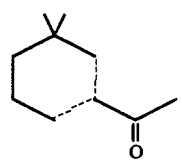

wherein are in fact in admixture and which are in fact compounds having the structures:

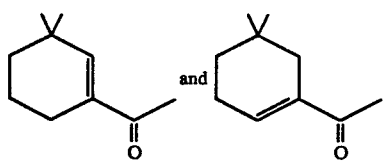

wherein the ratio of compound having the structure:

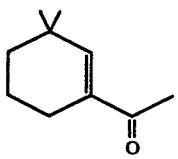

to the compound having the structure:

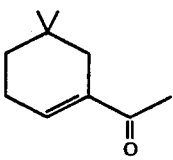

is from about 85:15 up to about 90:10.

The resulting mixture of compounds having the structures:

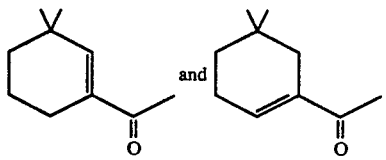

is then:

(i) reduced with a reducing agent according to the reaction:

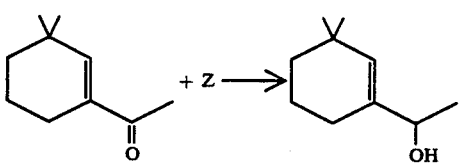

wherein Z is a reducing agent such as:

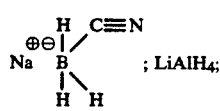

and $NaBH_4$ or (ii) reacted with a compound having the structure:

$CH_3 Q$ according to the reaction:

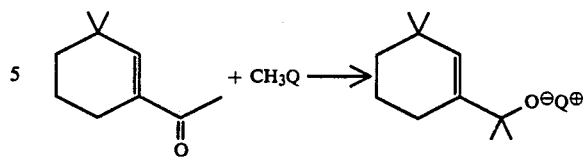

wherein Q is either Li or MgX wherein X is chloro or bromo to form the mixture of compounds having the structures:

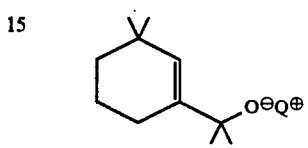

and

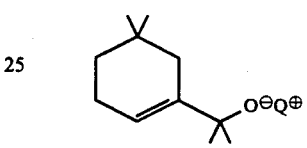

which is then hydrolyzed in acid to form the mixture of compounds having the structures:

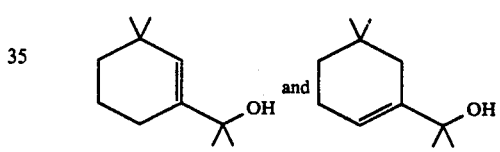

with the ratio of compound having the structure:

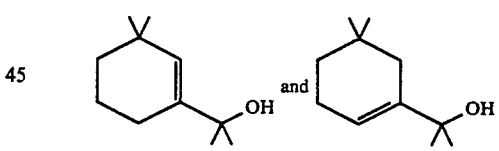

to the compound having the structure:

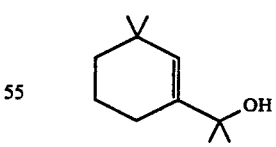

being from 85:15 up to 90:10.

The mixture of compounds having the structures:

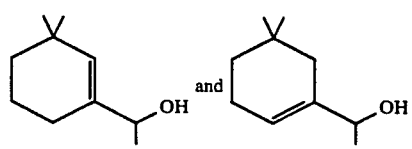

may, if desired, be further reacted with an acylating agent such as acetic anhydride according to the reaction:

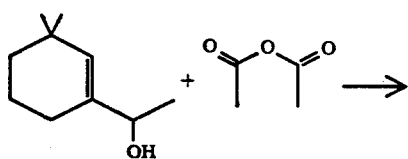

whereby the compounds having the structures:

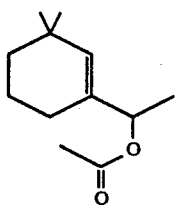

are formed with the ratio of compound having the structure:

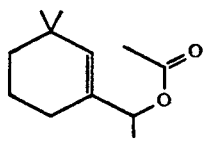

to the compound having the structure:

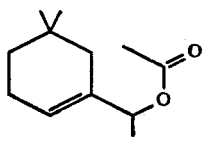

being from 85:15 up to 90:10.

The attempt to react the mixture of compounds having the structures:

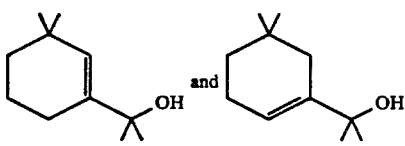

with acetic anhydride did not result in the corresponding acetate drivative.

The reaction, to wit:

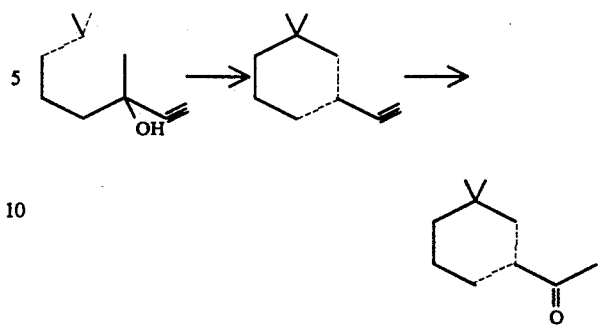

is carried out according to the conditions taught by Belgian Patent No. 852,918 published on Jul. 18, 1977 or Italian Patent 1,058,547 published on May 10, 1982 at a temperature in the range of from about 50° C. up to about 170° C. in the presence of phosphoric acid or polyphosphoric acid and, preferably, in the presence of a solvent such as toluene. Indeed, the product which is a mixture of compounds having the structures:

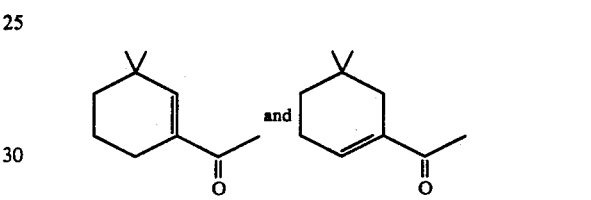

is marketed by Givaudan-Roure of Wayne, N.J. under the trademark "ARTEMONE ®".

The subsequent reduction according to the reaction:

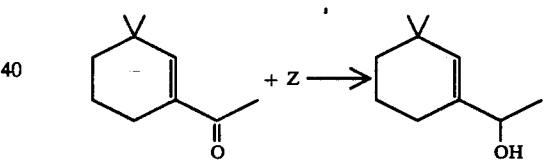

where Z is a reducing agent which is preferably one of the materials:

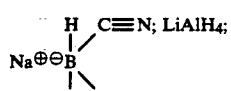

or

NaBH₄ is carried out at a temperature of from about 50° up to about 70° C. in the presence of an inert aqueous solvent such as aqueous isopropyl alcohol.

The subsequent reaction (if desired), to wit:

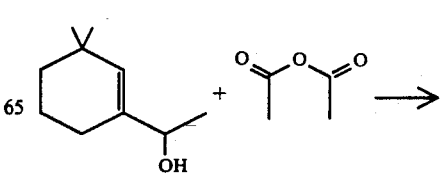

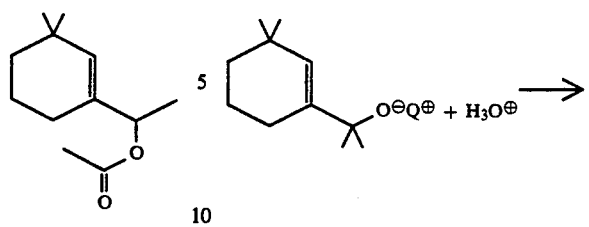

is carried out in the presence of an esterification catalyst, preferably paratoluene sulfonic acid; preferably at a temperature in the range of from about 60° C. up about to 80° C.

Examples of the reduction reaction are set forth as follows:

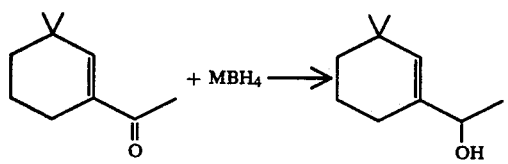

(wherein M represents sodium or potassium) and

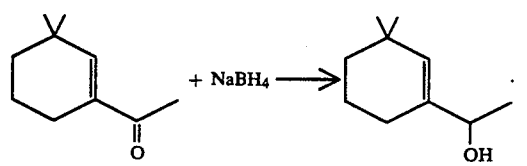

The reaction:

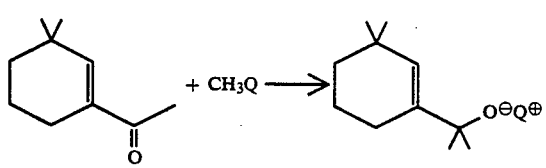

is carried out at temperatures in the range of from about −5° C. up to about +5° C. in the presence of an inert solvent such as diethyl ether or tetrahydrofuran. The mixture of salts having the structures:

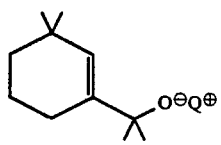

and

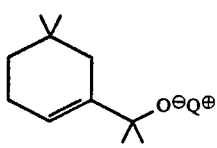

is then subjected to hydrolysis with acid (e.g., aqueous hydrochloric acid or aqueous sulfuric acid) according to the reaction:

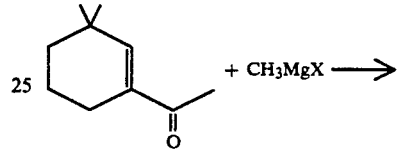

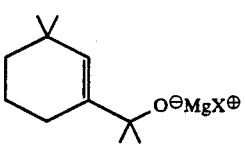

The hydrolysis reaction is carried out at a pH of from about 2 up to about 5. Other acids which may be used are, for example, acetic acid. Examples of the methylation reaction are as follows:

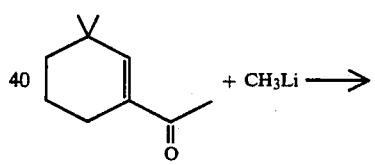

and

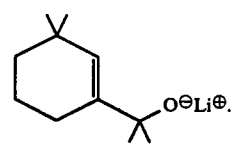

Examples of the hydrolysis reaction are as follows:

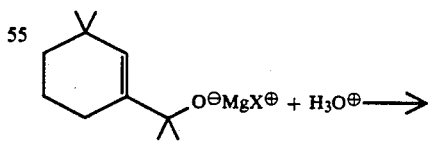

and

-continued

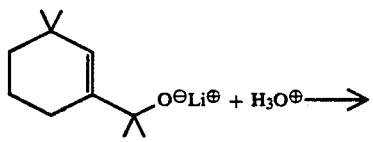

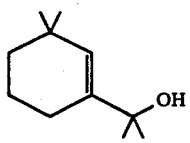

wherein X represents chloro or bromo and Q represents Li or MgX.

In all cases the resulting reaction product is distilled via fractional distillation and the final product is then utilized as indicated, infra, for augmenting, enhancing or imparting fragrance nuances to perfume compositions, colognes and perfumed articles.

The following Table I sets forth the products of my invention and their perfumery properties.

TABLE I

| Structure of Product of My Invention | Perfumery Property |
|---|---|
| Mixture of Compounds having the structures: [structure] and [structure] (ratio of compound having the structure: [structure] to compound having the structure: [structure] being 85:15) prepared according to Example I. | A rose, camphoraceous and fruity aroma with rose, apple, amber and animalic topnotes. |
| Mixture of compounds having the structures: [structure] and [structure] (with the ratio of compound having the structure: [structure] to the compound having the structure: [structure] being 85:15) prepared according to Example II. | A fruity, woody, green and patchouli aroma with green and woody undertones. |
| Mixture of compounds having the structures: [structure] and [structure] (with the ratio of compound having the structure: [structure] to the compound having the structure: [structure] being 85:15) prepared according to Example III. | A green, earthy and minty aroma profile. |

One or more of the alpha, 3,3-trimethyl-1-cyclohexen-1-methanol derivative-containing composition prepared in accordance with the processes of my invention and one or more auxiliary perfume ingredients including, for example, alcohols (other than the alcohols of my invention), aldehydes, ketones (other than the ketones of my invention), terpenic hydrocarbons, nitriles, esters (other than the esters of my invention), lactones, natural essential oils and synthetic essential oils may be admixed so that the combined odors of the individual components produce a pleasant and desired fragrance, particularly and preferably in the woody, minty, herbaceous, spicy and tagette fragrances. Such compositions usually contain:

(a) the main note or the "bouquet" or foundation stone of the composition;
(b) modifers which round-off and accompany the main note;
(c) fixatives which include odorous substances which lend a particular note to the perfume throughout all stages of evaporation and substances which retard evaporation; and
(d) topnotes which are usually low boiling, fresh smelling materials.

In perfume compositions, it is the individual components which contribute their particular olfactory characteristics, however, the overall sensory effect of the perfume composition will be at least the sum total of the effects of each of the ingredients. Thus, the alpha, 3,3-trimethyl-1-cyclohexen-1-methanol derivative-containing composition of my invention can be used to alter, modify or enhance the aroma characteristics of a perfume composition, for example, by utilizing or moderating the olfactory reaction contributed by another ingredient in the composition.

The amount of the alpha, 3,3-trimethyl-1-cyclohexen-1-methanol derivative-containing composition prepared in accordance with the processes of my invention which will be effective in perfume compositions as well as in perfumed articles (e.g., anionic, cationic, nonionic or zwitterionic detergents, soaps, fabric softener compositions, fabric softener articles and perfumed polymers) and colognes depends upon many factors including the other ingredients, their amounts and the effects which are desired. It has been found that perfume compositions containing as little as 0.01% of the alpha, 3,3-trimethyl-1-cyclohexen-1-methanol derivative-containing composition prepared in accordance with the processes of my invention or even less (e.g., 0.005%) can be used to impart, augment or enhance rose, camphoraceous, fruity, woody, green, patchouli, earthy and minty aromas, with rose, apple, amber and animalic topnotes and green and woody undertones to soaps, cosmetics, anionic, cationic, nonionic or Zwitterionic detergents, fabric softener articles, microporous polymers, particularly acrylic resins, polyethylenes and other products. The amount employed can range up to 70% of the fragrance components and will depend on considerations of cost, nature of the end product, the effect desired on the finished product and the particular fragrance sought.

The alpha, 3,3-trimethyl-1-cyclohexen-1-methanol derivative-containing composition of my invention are useful (taken alone or together with other ingredients in perfume compositions) as (an) olfactory component(s) in detergents and soaps, space odorants and deodorants, perfumes, colognes, toilet water, bath preparations such as creams, deodorants, hand lotions and sun screens; powders, such as talcs, dusting powders, face powders, microporous "perfumed" slow release polymers and the like.

When used as (an) olfactory component(s) in perfumed articles, as little as 0.005% of the alpha, 3,3-trimethyl-1-cyclohexen-1-methanol derivative-containing composition prepared in accordance with the processes of my invention will suffice to impart, augment or enhance rose, camphoraceous, fruity, woody, green, patchouli, earthy and minty aromas, with rose, apple, amber and animalic topnotes and green and woody undertones. Generally, no more than 6% of the alpha, 3,3-trimethyl-1-cyclohexen-1-methanol derivative-containing composition of my invention based on the ultimate end product is required in the perfumed article. Accordingly, the range of use of the alpha, 3,3-trimethyl-1-cyclohexen-1-methanol derivative-containing composition of my invention in perfumed articles, per se, is from about 0.005% up to about 6% by weight of the perfumed article.

In addition, the perfume composition or fragrance composition of my invention can contain a vehicle or carrier for the alpha, 3,3-trimethyl-1-cyclohexen-1-methanol derivative-containing composition prepared in accordance with the processes of my invention. The vehicle can be a liquid such as a non-toxic alcohol, e.g., ethyl alcohol, a non-toxic glycol, e.g., propylene glycol or the like. The carrier can be an absorbent solid such as a gum (e.g., gum arabic, guar gum or xanthan gum or a combination thereof) or components for encapsulating the composition (such as by coacervation) using prepolymers such as urea-formaldehyde prepolymers which are able to form a urea-formaldehyde polymer capsule around a liquid perfume center.

It will thus be apparent that the alpha, 3,3-trimethyl-1-cyclohexen-1-methanol derivative-containing composition of my invention can be utilized to alter, modify or enhance sensory properties particularly organoleptic properties such as fragrances of a wide variety of consumable materials.

The following Examples I, II and III set forth means for preparing the alpha, 3,3-trimethyl-1-cyclohexen-1-methanol derivative-containing composition of my invention. The examples including and following Example IV, infra, set forth illustrations of organoleptic utilities of the alpha, 3,3-trimethyl-1-cyclohexen-1-methanol derivative-containing composition of my invention.

All parts and percentages given herein are by weight unless otherwise specified.

EXAMPLE I

Preparation of Alpha, 3,3-Trimethyl-1-Cyclohexen-1-Methanol-Containing Composition Reaction:

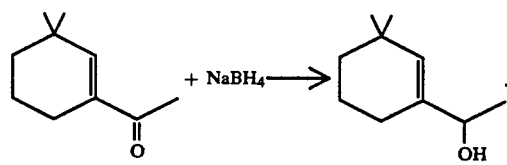

Into a 1.5 liter reaction vessel equipped with stirrer, thermometer and reflux condenser are placed 1 liter of isopropyl alcohol, 100 ml water and 180 grams of sodium borohydride.

The reaction mass is stirred for 1.5 hours at room temperature.

Over a period of 20 minutes, 1000 grams of a mixture of compounds having the structures:

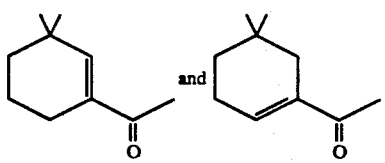

(85% by weight of the compound having the structure:

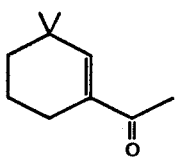

and 15% by weight of the compound having the structure:

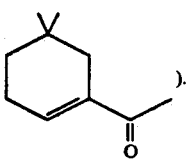

).

The reaction mass exotherms to 90° C. The reaction mass is cooled down to 60° C. The reaction mass is maintained at 60°–70° C. for an additional hour.

The reaction mass is then washed with an equal volume of 5% sodium hydroxide followed by an equal volume of water.

The reaction mass is then filtered and distilled on a "Rushover" column yielding the following fractions:

| Fraction No. | Vapor Temp. (°C.) | Liquid Temp. (°C.) | Vacuum mm/Hg. Pressure |
|---|---|---|---|
| 1 | 67/ | 128/ | 350 |
| 2 | 64 | 128 | 100 |
| 3 | 90 | 114 | 8 |
| 4 | 93 | 113 | 8 |
| 5 | 94 | 113 | 8 |
| 6 | 104 | 113 | 8 |
| 7 | 107 | 115 | 8 |
| 8 | 105 | 123 | 8 |
| 9 | 104 | 165 | 8. |

Fraction 5 boiling at 95° C. at 8 mm/Hg. is then redistilled on a 1.5×12" Goodloe column yielding the following fractions:

| Fraction No. | Vapor Temp. (°C.) | Liquid Temp. (°C.) | Vacuum mm/Hg. Pressure |
|---|---|---|---|
| 1 | 69/ | 83/ | 2.4 |
| 2 | 63 | 80 | 2.3 |
| 3 | 63 | 81 | 2.3 |
| 4 | 64 | 80 | 2.4 |
| 5 | 64 | 80 | 2.4 |
| 6 | 63 | 80 | 2.2 |
| 7 | 63 | 80 | 2.1 |
| 8 | 63 | 80 | 2.10 |
| 9 | 63 | 80 | 2.08 |
| 10 | 63 | 80 | 2.04 |
| 11 | 72 | 125 | 3.0 |
| 12 | 72 | 155 | 2.8 |
| 13 | 71 | 177 | 2.8. |

Figure 1:
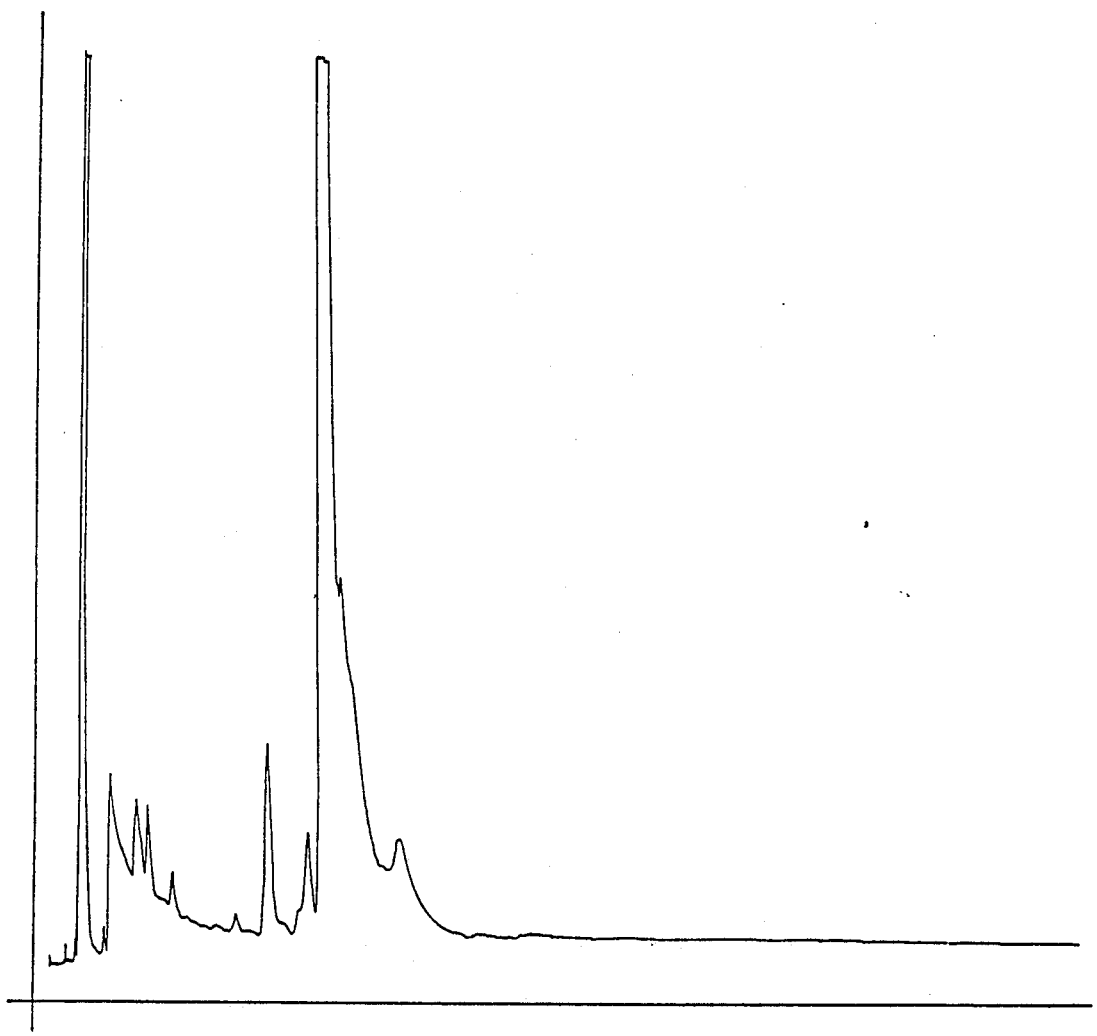
FIG. 1 is the GLC profile for the crude reaction product of Example I containing the compounds having the structures.

FIG. 1 is the GLC profile of the crude reaction product prior to distillation. FIG. 2 is the NMR spectrum for the compound having the structure:

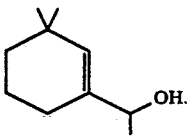

The resulting product has a rose, camphoraceous and fruity aroma with rose, apple, amber and animalic topnotes. The resulting product is 85% of the compound having the structure:

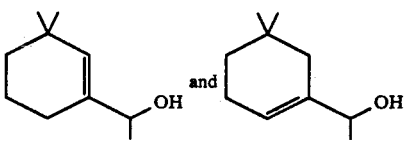

and 15% of the compound having the structure:

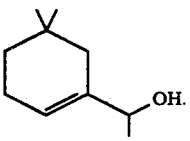

EXAMPLE II

Preparation of the Acetate Ester of Alpha, 3,3-Trimethyl-1-Cyclohexen-1-Methanol Reaction:

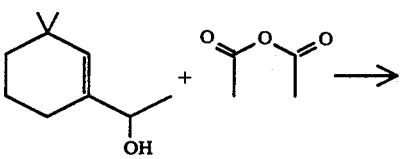

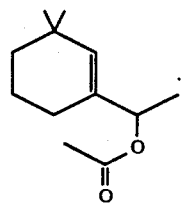

Into a 1 liter reaction vessel equipped with stirrer, thermometer and reflux condenser are placed 179 grams of bulked distillation fractions 1–3 of the reaction product of Example I containing the compounds having the structures:

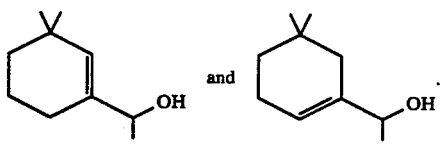

Also added to the reaction vessel are 1225 grams of acetic anhydride, 500 ml toluene and 0.29 grams of paratoluene sulphonic acid.

With stirring, the reaction mass is heated to 60° C. and maintained at 60° C. with stirring for a period of 13 hours.

The reaction mass is then poured into water and washed with sodium carbonate to a pH of 8.

The reaction mass is then rushed over on a "Rushover" column yielding the following fractions:

| Fraction No. | Vapor Temp. (°C.) | Liquid Temp. (°C.) | Vacuum mm/Hg. Pressure |
|---|---|---|---|
| 1 | 50/ | /94 | 73 |
| 2 | 76 | 96 | 53 |
| 3 | 94 | 109 | 32 |
| 4 | 106 | 112 | 18 |
| 5 | 100 | 112 | 9 |
| 6 | 98 | 118 | 9 |
| 7 | 98 | 125 | 6. |

Fractions 4 and 5 are bulked and redistilled on a 1"×10" distillation column yielding the following fractions:

| Fraction No. | Vapor Temp. (°C.) | Liquid Temp. (°C.) | Vacuum mm/Hg. Pressure |
|---|---|---|---|
| 1 | 43/62 | 75/78 | 1.6 |
| 2 | 75 | 83 | 3.0 |
| 3 | 75 | 83 | 2.8 |
| 4 | 62 | 83 | 1.3 |
| 5 | 65 | 78 | 1.55 |
| 6 | 68 | 80 | 1.55 |
| 7 | 72 | 82 |  |
| 8 | 71 | 85 | 2.0 |
| 9 | 80 | 94 | 3.3 |
| 10 | 90 | 110 | 4.4 |
| 11 | 90/72 | 182 | 4.3. |

The resulting product which is a mixture of compound having the structures:

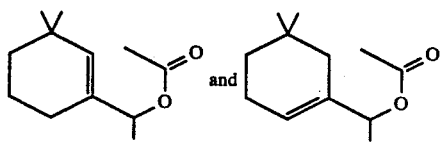

has a fruit, woody, green and patchouli aroma with green and woody undertones. It contains 85% by weight of the compound having the structure:

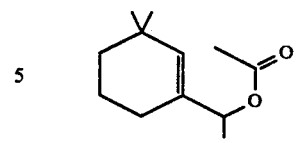

and 15% by weight of the compound having the structure:

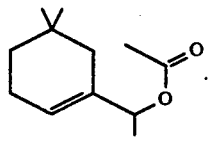

FIG. 3 is the GLC profile for the crude reaction product prior to distillation. The peak indicated by reference numeral 30 is the peak for the mixture of compounds having the structures:

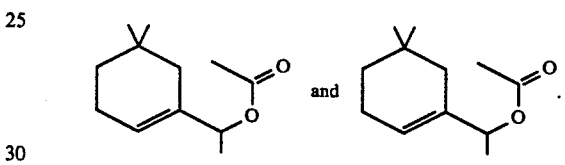

The peaks indicated by reference numerals 32 and 34 are the peaks for the compounds having the structures:

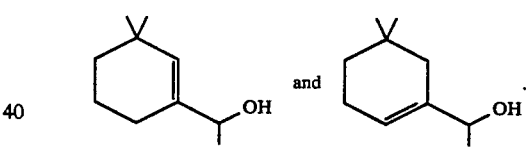

the starting materials. FIG. 4 is the NMR spectrum for the compound having the structure:

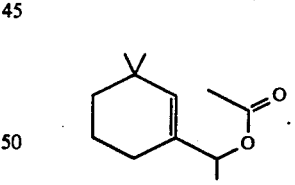

EXAMPLE III

Preparation of Alpha, Alpha, 3,3-Tetramethyl-1-Cyclohexen-1-Methanol

Reactions:

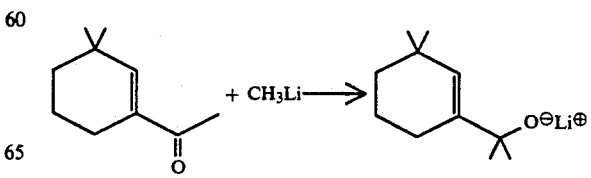

and

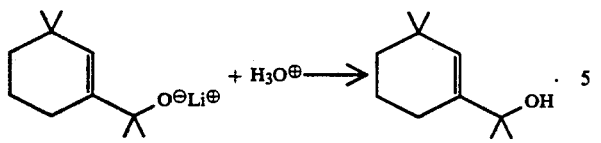

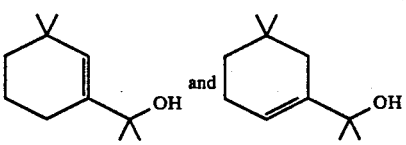

wherein the compound having the structure:

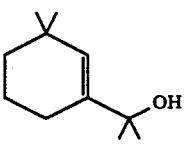

is in an amount of 85% by weight of the mixture and the compound having the structure:

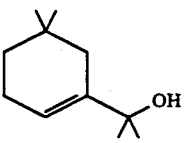

Into a 3 liter reaction vessel equipped with stirrer, thermometer and reflux condenser are placed 1800 ml of a solution of methyl lithium in diethyl ether. The solution is cooled to 0° C. and over a period of one hour while maintaining the temperature at 0° C., 300 grams of the mixture of compounds having the structures:

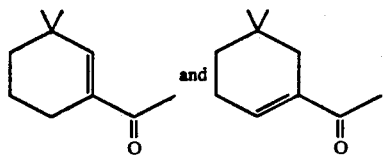

are added to the reaction mass with stirring. One liter of toluene is also added to the reaction mass with stirring at this point in time. The reaction mass is then stirred for a period of three hours while maintaining the reaction mass at 0°-10° C.

The reaction mass is then quenched with 200 grams of a mixture of 100 grams of acetic acid and 100 grams of water.

The reaction mass is then washed with 1 liter of saturated sodium bicarbonate followed by 1 liter of water to a pH of 8. The reaction mass is then rushed over on a "Rushover" column yielding the following fractions:

is in an amount of 15% by weight of the mixture. The resulting mixture has a green, earthy and minty aroma profile.

FIG. 5 is the GLC profile for the crude reaction product.

FIG. 6 is the GLC profile for bulked distillation fractions 2-5. The peak indicated by reference numeral 60 is the peak for the mixture of compounds having the structures:

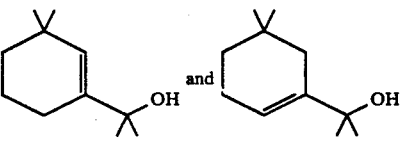

| Fraction No. | Vapor Temp. (°C.) | Liquid Temp. (°C.) | Vacuum mm/Hg. Pressure |
|---|---|---|---|
| 1 | 35/77 | 88/84 | 1.5/0.8 |
| 2 | 84 | 84 | 8.0 |
| 3 | 82 | 83 | 5.4 |
| 4 | 88 | 90 | 8.0 |
| 5 | 88 | 92 | 8.1 |
| 6 | 94 | 108 | 9.0 |
| 7 | 95 | 118 | 10.0 |
| 8 | 90 | 138 | 10.8. |

Fractions 3, 4, 5, 6, 7 and 8 are bulked and redistilled on a 1"×10"Goodloe column yielding the following fractions:

wherein the compound having the structure:

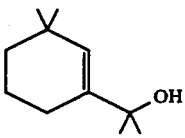

is in an amount of 85% by weight and the compound having the structure:

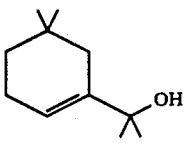

| Fraction No. | Vapor Temp. (°C.) | Liquid Temp. (°C.) | Vacuum mm/Hg. Pressure |
|---|---|---|---|
| 1 | 75/ | 92/ | 6.8 |
| 2 | 68 | 83 | 2.4 |
| 3 | 67 | 83 | 2.6 |
| 4 | 67 | 83 | 2.5 |
| 5 | 67 | 83 | 2.7 |
| 6 | 64 | 82 | 2.4 |
| 7 | 75 | 85 | 21.8 |
| 8 | 75 | 88 | 2.5 |
| 9 | 78 | 90 | 2.8 |
| 10 | 80 | 102 | 2.8 |
| 11 | 85 | 160 | 2.8 |
| 12 | 84 | 170 | 2.8. |

Fractions 3-5 are bulked. Bulked distillation fractions 3-5 contain the compounds having the structures:

is in an amount of 15% by weight.

FIG. 7 is the NMR spectrum for the compound having the structure:

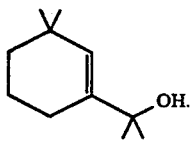

EXAMPLE IV

Perfume Formulations

The following woody cologne perfume formulations are prepared:

| Ingredients | Parts by Weight | | |
|---|---|---|---|
| | IV(A) | IV(B) | IV(C) |
| Bergamot oil | 150 | 150 | 150 |
| Orange oil | 200 | 200 | 200 |
| Lemon oil | 50 | 50 | 50 |
| Eugenol | 10 | 10 | 10 |
| 4-(4-Methyl-4-hydroxy amyl Delta³cyclohexene carboxaldehyde (LYRAL ® Trademark of International Flavors & Fragrances Inc. of New York, New York) | 40 | 40 | 40 |
| Ylang oil | 2 | 2 | 2 |
| Petigrain Paraguay | 10 | 10 | 10 |
| Gamma-Methyl ionone | 20 | 20 | 20 |
| Vetiver Venezuela | 18 | 18 | 18 |
| 3-Alpha-Methyl-dodecahydro-6,6,9a-trimethylnaptho[2,1-b]furan | 5 | 5 | 5 |
| Product produced by the reaction of acetic anhydride polyphosphoric acid and 1,5,9-trimethyl cyclododecatriene-1,5,9 according to the process of Example I of U.S. Letters Pat. No. 3,718,697, the specification for which is incorporated by reference herein | 50 | 50 | 50 |
| Octahydro-9,9-dimethyl-1,6-methanonaphthalene-1-[2H]-ol produced according to Example III of U.S. Letters Pat. No. 3,996,169, the specification for which is incorporated by reference herein | 50 | 50 | 50 |
| Mixture of compounds having the structures: 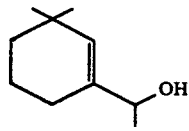 and 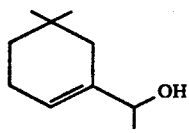 produced according to Example I (wherein the weight percent of compound having the structure: 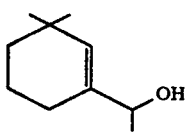 and the weight percent of compound having the structure: | 12 | 0 | 0 |

| Ingredients | Parts by Weight | | |
|---|---|---|---|
| | IV(A) | IV(B) | IV(C) |
| is 15%). Mixture of compounds having the structures: and wherein the compound having the structure: is in an amount of 85% of the mixture and the compound having the structure: is in an amount of 15% by weight of the mixture. | 0 | 12 | 0 |
| Mixture of compounds having the structures: and (wherein the amount of compound in the mixture having the structure: is in an amount of 85% and the compound having the structure: is in an amount of 15%) | 0 | 0 | 12 |

-continued

| Ingredients | Parts by Weight | | |
|---|---|---|---|
| | IV(A) | IV(B) | IV(C) |
| producted according to Example III. | | | |

The mixture of compounds having the structures:

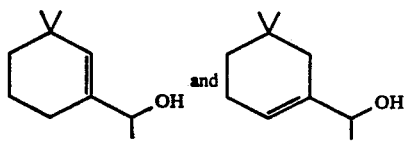

produced according to Example I imparts to this woody cologne perfume, rose, camphoraceous and fruity undertones, with rose, apple, amber and animalic topnotes. Accordingly, the perfume composition of Example IV(A) can be described as "woody cologne with rose, camphoraceous and fruity undertones and rose, apple, amber and animalic topnotes".

The mixture of compounds having the structures;

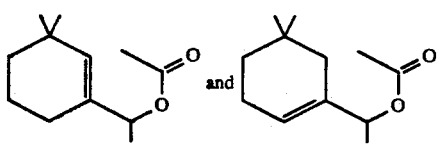

produced according to Example II imparts to this woody cologne perfume formulation woody, fruity, green and patchouli topnotes, with green and woody undertones. Accordingly, the formulation of Example IV(B) can be described as "woody cologne, with green and woody undertones and woody, green, fruity and patchouli topnotes".

The mixture of compounds having the structures:

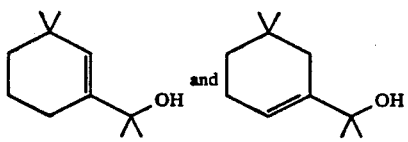

Prepared according to Example III imparts to this woody cologne formulation green, earthy and minty undertones. Accordingly, the formulation of Example IV(C) can be described as "woody cologne with green, earthy and minty undertones".

EXAMPLE VI

Preparation of Cosmetic Powder Composition

Cosmetic powder compositions are prepared by mixing in a ball mill 100 grams of talcum powder with 0.25 grams of each of the substances set forth in Table II below. Each of the cosmetic powder compositions has an excellent aroma as described in Table II below:

TABLE II

| Substance | Aroma Description |
|---|---|
| Mixture of compounds having the structures: [structure with OH] and [structure with OH] wherein the percentage of compound having the structure: [structure with OH] is 85% and the percentage of compound having the structure: [structure with OH] is 15% prepared according to Example I. | A rose, camphoraceous and fruity aroma, with rose, apple, amber and animalic topnotes. |
| [structure with ester group] and [structure with ester group] prepared according to Example II, wherein the compound having the structure: [structure with ester] is present in an amount of 85% and the compound having the structure: [structure with ester] is present in an amount of 15%. | A fruity, woody, green and patchouli aroma profile, with green and woody undertones. |
| Mixture of compounds having the structures: | A green, earthly and minty aroma profile. |

TABLE II-continued

| Substance | Aroma Description |
|---|---|
| 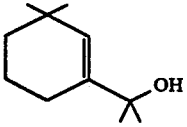<br>and<br>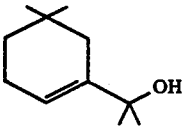<br>prepared according to Example III, wherein the compound having the structure:<br>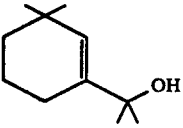<br>is present in an amount of 85% and the compound having the structure:<br>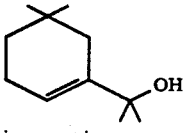<br>is present in an amount of 15%.<br>Perfume composition of Example IV(A). | Woody cologne, with rose, camphoraceous and fruity undertones and rose, apple, amber and animalic topnotes. |

EXAMPLE VI

Perfumed Liquid Detergents

Concentrated liquid detergents (Lysine salt of n-dodecyl-benzene sulfonic acid as more specifically described in U.S. Pat. No. 3,948,818 issued on Apr. 6, 1976 incorporated by reference herein) with aroma nuances as set forth in Table II of Example V are prepared containing 0.10%, 0.15%, 0.2%, 0.25%, 0.3% and 0.35% of the substance set forth in Table II of Example V. They are prepared by adding and homogeneously mixing the appropriate quantity of substance set forth in Table II of Example V in the liquid detergent. The detergents all possess excellent aromas as set forth in Table II of Example V, the intensity increasing with greater concentrations of substances as set forth in Table II of Example V.

EXAMPLE VII

Preparation of Colognes and Handkerchief Perfumes

Compositions as set forth in Table II of Example V are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definitive fragrances as set forth in Table II of Example V are imparted to the colognes and to the handkerchief perfumes at all levels indicated.

EXAMPLE VIII

Preparation of Soap Compositions

One hundred grams of soap chips [per sample](IVORY ®, produced by the Procter & Gamble Company of Cincinnati, Ohio), are each mixed with one gram samples of substances as set forth in Table II of Example V until homogeneous compositions are obtained. In each of the cases, the homogeneous compositions are heated under 8 atmospheres pressure at 180° C. for a period of three hours and the resulting liquids are placed into soap molds. The resulting soap cakes, on cooling manifest aromas as set forth in Table II of Example V.

EXAMPLE IX

Preparation of Solid Detergent Compositions

Detergents are prepared using the following ingredients according to Example I of Canadian Patent No. 1,007,948 (incorporated by reference herein):

| Ingredient | Percent by Weight |
|---|---|
| "NEODOL" ® 45-11 (a $C_{12}$-$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a phosphate-free detergent. Samples of 100 grams each of this detergent are admixed with 0.10, 0.15, 0.20 and 0.25 grams of each of the substances as set forth in Table II of Example V. Each of the detergent samples has an excellent aroma as indicated in Table II of Example V.

EXAMPLE X

Utilizing the procedure of Example I at column 15 of U.S. Pat. No. 3,632,396 (the disclosure of which is incorporated herein by reference), non-woven cloth substrates useful as drier-added fabric softening articles of manufacture are prepared wherein the substrate, the substrate coating, the outer coating and their perfuming material are as follows:
1. A water "dissolvable" paper ("Dissolvo Paper");
2. Adogen 448 (m.p. about 140° F.) as the substrate coating; and
3. An outer coating having the following formulation (m.p. about 150° F.);
   57% $C_{20-22}$ HAPS;
   22% isopropyl alcohol;
   20% antistatic agent; and
   1% of one of the substances as set forth in Table II of Example V.

Fabric softening compositions prepared according to Example I at column 15 of U.S. Pat. No. 3,632,396 having the aroma characteristics as set forth in Table II of Example V, supra, consist of a substrate coating having a weight of about 3 grams per 100 square inches of substrate a first coating located directly on the substrate coating consisting of about 1.85 grams per 100 square inches of substrate; and an outer coating coated on the first coating consisting of about 1.4 grams per 100 square inches of substrate. One of the substances of Table II of Example V is admixed in each case with the outer coating mixture, thereby providing a total aromatized outer coating weight ratio to substrate of about 0.5:1 by weight of the substrate. The aroma characteristics are imparted in a pleasant manner to the head space in a dryer on operation thereof in each case using said drier-added fabric softener non-woven fabrics and these aroma characteristics are described in Table II of Example V, supra.

EXAMPLE XI

Hair Spray Formulations

The following hair spray formulation is prepared by first dissolving PVP/VA E-735 copolymer manufactured by the GAF Corporation of 140 West 51st Street, New York, N.Y., in 91.62 grams of 95% of food grade ethanol, 8.0 grams of the polymer is dissolved in the alcohol. The following ingredients are added to the PVP/VA alcoholic solution:

| Ingredient | Percent by Weight |
|---|---|
| Dioctyl sebacate | 0.05 |
| Benzyl alcohol | 0.10 |
| Dow Corning 473 fluid (prepared by the Dow Corning Corporation) | 0.10 |
| TWEEN ® 20 surfactant prepared by ICI America Corporation | 0.03 |
| One of the perfumery substances as set forth in Table II of Example V supra. | 0.10 |

The perfuming substances as set forth in Table II of Example V add aroma characteristics as set forth in Table II of Example V which are rather intense and aesthetically pleasing to the users of the soft-feel, good-hold pump hair sprays.

EXAMPLE XII

Conditioning Shampoos

Monamid CMA (prepared by the Mona Industries Company)(3.0 weight percent) is melted with 2.0 weight percent coconut fatty acid (prepared by Procter & Gamble Company of Cincinnati, Ohio); 1.0 weight percent ethylene glycol distearate (prepared by the Armak Corporation) and triethanolamine (a product of Union Carbide Corporation)(1.4 weight percent). The resulting melt is admixed with Stepanol WAT produced by the Stepan Chemical Company (35.0 weight percent). The resulting mixture is heated to 60° C. and mixed until a clear solution is obtained (at 60° C.). This material is "COMPOSITION A".

GAFQUAT 755N polymer (manufactured by GAF Corporation of 140 West 51st Street, New York, N.Y.)(5.0 weight percent) is admixed with 0.1 weight percent sodium sulfite ad 1.4 weight percent polyethylene glycol 6000 distearate produced by Armak Corporation. This material is "COMPOSITION B".

The resulting "COMPOSITION A" and "COMPOSITION B" are then mixed in a 50:50 weight ratio of A:B and cooled to 45° C. and 0.3 weight percent of perfuming substance as set forth in Table II of Example V is added to the mixture. The resulting mixture is cooled to 40° C. and blending is carried out for an additional one hour in each case. At the end of this blending period, the resulting material has a pleasant fragrance as indicated in Table II of Example V.

What is claimed is:

1. A process comprising the steps of:
   (i) reacting a mixture of compounds defined according to the structure:

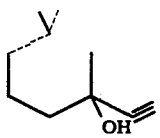

with a dehydrating agent selected from the group consisting of phosphoric acid and polyphosphoric acid at a temperature in the range of from about 50° C. up to 170° C. in order to carry out the reaction:

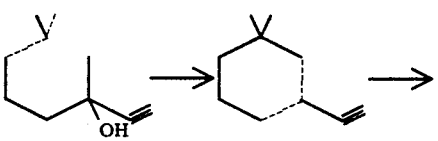

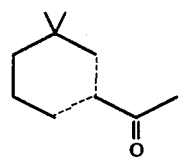

wherein in each of the compounds of the mixtures, one of the dashed lines represents a carbon-carbon double bond and the other of the dashed lines represents a carbon-carbon single bond, wherein the compound shown as the structure:

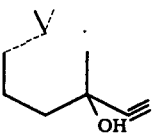

consists of two materials having the structures:

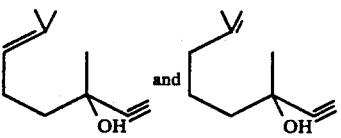

and wherein the resulting product shown as the structure:

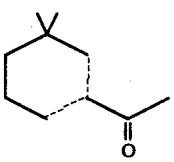

is a mixture of two compounds having the structures:

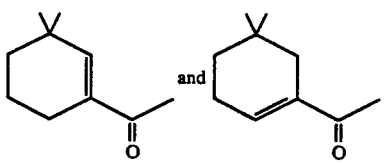

wherein the compound having the structure:

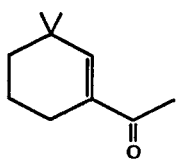

is present in the reaction product in an amount from 85-90% by weight and the compound having the structure:

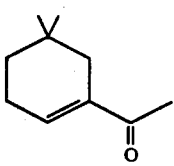

is present in the reaction product in an amount of from 10-15% by weight;
(ii) then either:
(a) reducing the mixture of compound having the structures:

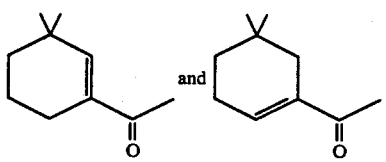

using a reducing agent selected from the group consisting of compounds having the structures:

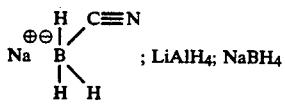; LiAlH$_4$; NaBH$_4$ at a temperature of from about 50° C. up to about 70° C. in the presence of an inert aqueous solvent according to the reaction:

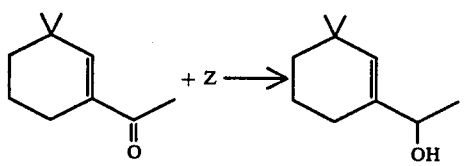

wherein Z is a material selected from the group consisting of:

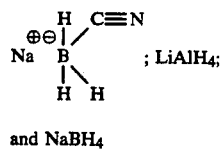; LiAlH$_4$;

and NaBH$_4$ whereby a mixture of compounds is produced having the structures:

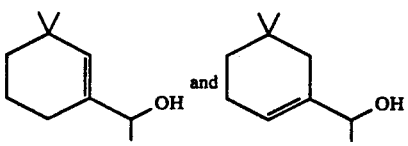

wherein the compound having the structure:

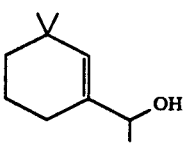

is present in an amount of from 85-90% and the compound having the structure:

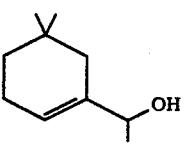

is present in an amount of from 10-15%; or
(b) reacting the mixture of compounds having the structures:

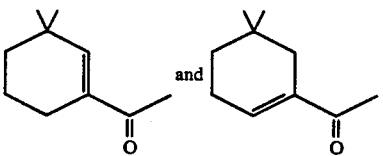

with a compound having the structure:

CH$_3$Q, wherein Q represent Li or MgX and X represents chloro or bromo, according to the reaction: according to the reaction:

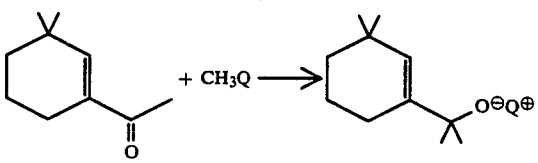

at a temperature in the range of from about −5° C. up to about +5° C. in the presence of an inert solvent and then hydrolyzing the resulting product at a pH of from about 2 up to about 5 according to the reaction:

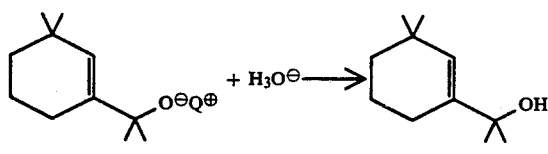

whereby a mixture of compounds having the structures:

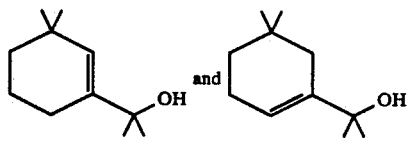

is produced wherein the compound having the structure:

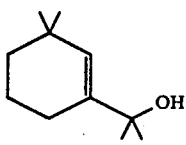

is present in the reaction mass in an amount of from 85-90% and the compound having the structure:

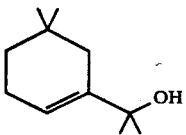

is present in the reaction mass in an amount of from 10-15%; and (iii) optionally, reacting the mixture of compounds having the structures:

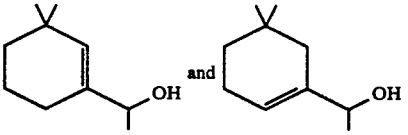

with an acetylating agent according to the reaction:

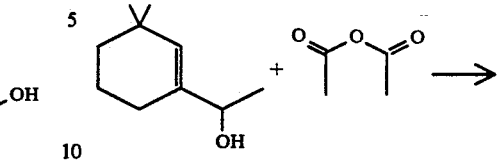

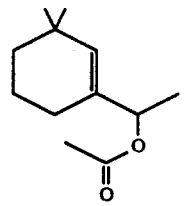

in the presence of an esterification catalyst at a temperature in he range of from about 60° C. up to about 80° C. whereby a mixture compounds having the structures:

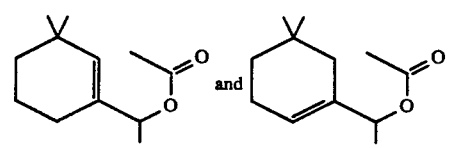

is produced wherein, in the mixture the compound having the structure:

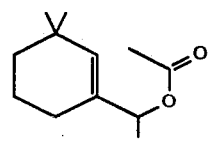

is present in an amount of from 85-90% and the compound having the structure:

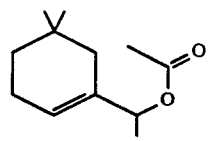

is present in an amount of from 10-15%.

* * * * *